United States Patent
Tanaka

(10) Patent No.: US 8,143,065 B2
(45) Date of Patent: Mar. 27, 2012

(54) SPECIMEN PROCESSING DEVICE, SPECIMEN CONVEYANCE DEVICE, AND SPECIMEN CONVEYANCE METHOD

(75) Inventor: Hiroyuki Tanaka, Halstenbek (DE)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 12/587,185

(22) Filed: Oct. 2, 2009

(65) Prior Publication Data

US 2010/0083772 A1 Apr. 8, 2010

(30) Foreign Application Priority Data

Oct. 6, 2008 (JP) ................................. 2008-259267

(51) Int. Cl.
*G01N 35/02* (2006.01)
*G01N 35/00* (2006.01)

(52) U.S. Cl. ............ 436/47; 436/43; 73/863.91; 73/863

(58) Field of Classification Search .................... 436/47, 436/43; 73/863.91, 863
See application file for complete search history.

(56) References Cited

U.S. PATENT DOCUMENTS 6,290,907 B1 9/2001 Takahashi et al.
2005/0036912 A1* 2/2005 Yamakawa et al. ............. 422/65

* cited by examiner

*Primary Examiner* — Christine T Mui
(74) *Attorney, Agent, or Firm* — Brinks Hofer Gilson & Lione

(57) ABSTRACT

A specimen processing device comprising: a specimen processing unit for processing specimens; a first conveyance mechanism for conveying specimens from a carry-in side towards a carry-out side on the opposite side of the carry-in side with respect to the specimen processing unit through a specimen supply position for supplying specimens to the specimen processing unit; a second conveyance mechanism for conveying specimens from the carry-in side towards the carry-out side without passing the specimen supply position; a first control device for controlling the first conveyance mechanism; and a second control device for controlling the second conveyance mechanism, is disclosed. A specimen conveyance device and a specimen conveyance method are also disclosed.

11 Claims, 14 Drawing Sheets

SPECIMEN PROCESSING DEVICE, SPECIMEN CONVEYANCE DEVICE, AND SPECIMEN CONVEYANCE METHOD

RELATED APPLICATIONS

This application claims priority under 35 U.S.C. §119 to Japanese Patent Application No. JP2008-259267 filed on Oct. 6, 2008, the entire content of which is hereby incorporated by reference.

FIELD OF THE INVENTION

The present invention relates to a specimen processing device for conveying a specimen and processing the conveyed specimen with a specimen processing unit, and a specimen conveyance device and a specimen conveyance method for conveying the specimen to supply the specimen to the specimen processing unit.

BACKGROUND

Conventionally, a specimen processing device, including a plurality of specimen processing units such as a specimen analyzing unit and a smear producing unit and a conveyance device for conveying the specimen to supply to the specimen processing unit, for conveying the specimen to each specimen processing unit by the conveyance device, and processing the conveyed specimen with the specimen processing unit is known.

U.S. Pat. No. 6,290,907 discloses a specimen processing system including a conveyance line for conveying a specimen rack for holding a specimen, a rack inserting unit, a rack accommodating unit, a centrifugal unit, a dispensing unit, an analyzing unit, an opening unit, a barcode labeler unit, a closing unit, and a plurality of specimen processing units such as a specimen classifying unit, wherein the conveyance line conveys the specimen rack holding the specimen in a manner the specimen rack can stop at the instructed processing unit. The conveyance line of the specimen processing system has a configuration in which a plurality of partial line units that respectively forms a pair with a plurality of processing units is connected in series, wherein if the processing unit is shutdown or in a maintenance state, the specimen rack advances to the next processing step without stopping at the relevant processing unit. The conveyance rack includes a main conveyance path, arranged between the rack inserting unit and the rack accommodating unit, for conveying the specimen rack from the rack inserting unit side towards the rack accommodating unit side, and return conveyance path for conveying the specimen rack, as necessary, from the rack accommodating unit side to the rack inserting unit side, wherein each partial line unit is partially in charge of the main conveyance path and the return conveyance path. Each partial line unit is built in with a unit controller for controlling the operation in the own unit.

However, in the specimen processing system described in U.S. Pat. No. 6,290,907, the partial line unit has a configuration of controlling the main conveyance path and the return conveyance path with one unit controller, and thus the entire partial line unit becomes inoperative when failure occurs in the unit controller, the main conveyance path, or the return conveyance path.

SUMMARY OF THE INVENTION

The scope of the present invention is defined solely by the appended claims, and is not affected to any degree by the statements within this summary.

A first aspect of the present invention is a specimen processing device comprising: a specimen processing unit for processing specimens; a first conveyance mechanism for conveying specimens from a carry-in side towards a carry-out side on the opposite side of the carry-in side with respect to the specimen processing unit through a specimen supply position for supplying specimens to the specimen processing unit; a second conveyance mechanism for conveying specimens from the carry-in side towards the carry-out side without passing the specimen supply position; a first control device for controlling the first conveyance mechanism; and a second control device for controlling the second conveyance mechanism.

A second aspect of the present invention is a specimen conveyance device comprising: a first conveyance mechanism for conveying a specimen from a carry-in side towards a carry-out side on the opposite side of the carry-in side with respect to a specimen processing unit through a specimen supply position for supplying specimens to the specimen processing unit; a second conveyance mechanism for conveying specimens from the carry-in side towards the carry-out side without passing the specimen supply position; a first control device for controlling the first conveyance mechanism; and a second control device for controlling the second conveyance mechanism.

A third aspect of the present invention is a specimen conveyance method executed in a specimen processing device including a first conveyance mechanism for conveying specimens through a specimen supply position for supplying specimens to a specimen processing unit for processing specimens, a second conveyance mechanism for conveying specimens without passing the specimen supply position, a first control device for controlling the first conveyance mechanism, and a second control device for controlling the second conveyance mechanism; comprising: (a) conveying specimens to a first conveyance region, on which specimens are conveyed by the first conveyance mechanism, by the second conveyance mechanism according to a control by the second control device; (b) conveying the specimens conveyed to the first conveyance region to a second conveyance region, on which specimens are conveyed by a second conveyance mechanism, through the specimen supply position by the first conveyance mechanism according to a control by the first control device; and (c) carrying out the specimens conveyed to the second conveyance region to a device on a downstream side of conveyance by the second conveyance mechanism according to the control by the second control device.

DETAILED DESCRIPTION OF THE PREFERRED EMBODIMENTS

The preferred embodiments of the present invention will be described hereinafter with reference to the drawings.

The present embodiment relates to a specimen processing device (specimen processing system), including a specimen analyzing unit (specimen analyzer) for analyzing a clinical specimen such as blood and urine, a first conveyance mechanism for conveying the specimen to supply the specimen to the specimen analyzer, a second conveyance mechanism for conveying the specimen not to supply the specimen to the specimen analyzer, an information processing unit for controlling the first conveyance mechanism, and a controller for controlling the second conveyance mechanism, wherein the information processing unit can control the first conveyance mechanism even while the controller is stopping the control operation.

(Configuration of Specimen Processing System)

Figure 1:
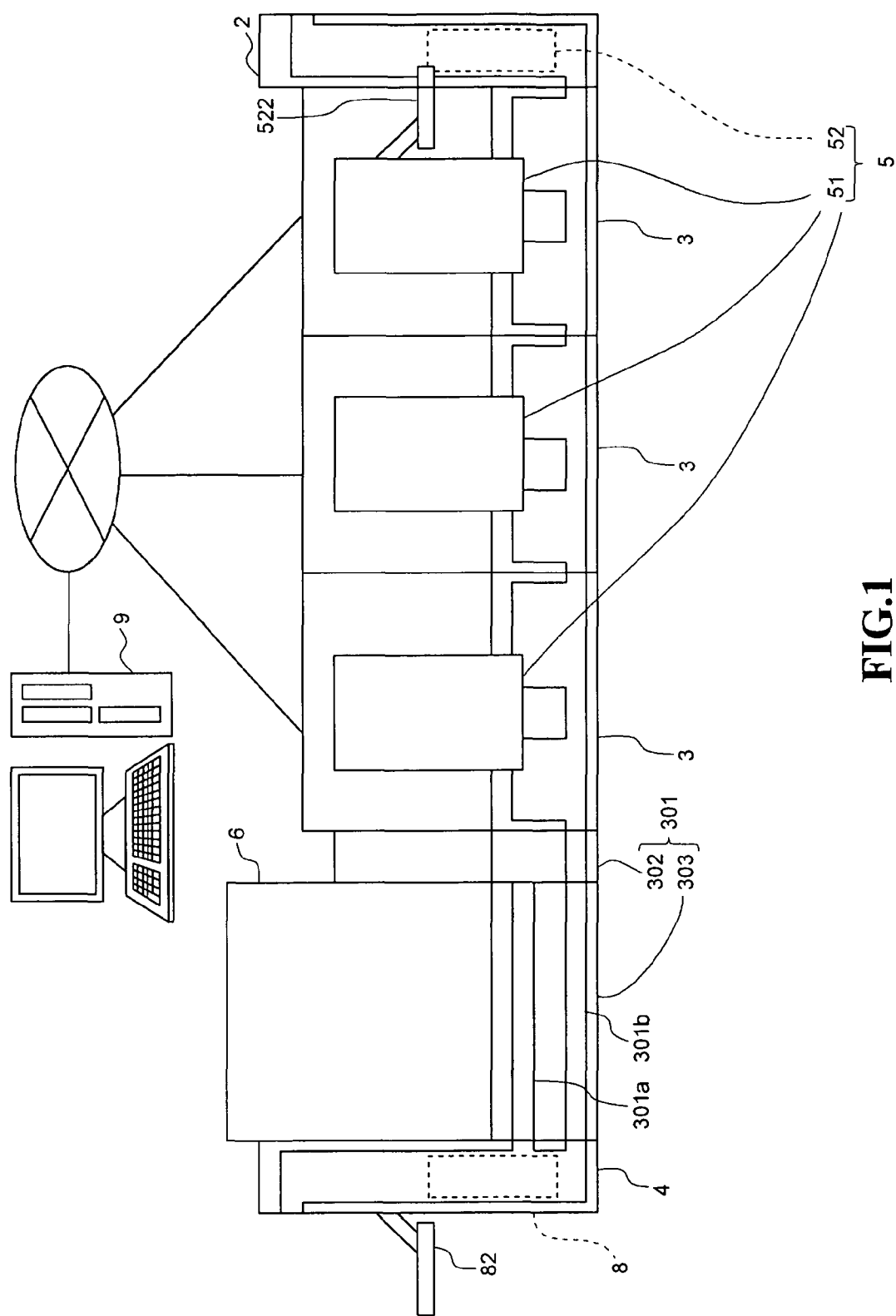
FIG. 1 is a schematic plan view showing an overall configuration of a specimen processing system according to an embodiment.

FIG. 1 is a schematic plan view showing an overall configuration of a specimen processing system according to the present embodiment. As shown in FIG. 1, the specimen processing system includes a specimen inserting device 2, specimen conveyance devices 3, 301, a specimen accommodating device 4, a blood cell analyzer 5, a smear producing device 6, and a system control device 8. The specimen processing system according to the present embodiment is communicably connected to a host computer 9 by way of a communication network.

<Configuration of Specimen Inserting Device 2>

The specimen inserting device 2 is configured such that a sample rack accommodating a plurality of specimen containers can be mounted. The specimen inserting device 2 includes a controller (not shown) configured by a CPU, a memory, and the like, a sending mechanism (not shown) for sending a sample rack, and a sensor (not shown) for detecting the mounted sample rack, wherein the sample rack mounted on the specimen inserting device 2 is detected by the sensor, and the sample rack detected by the sensor is sent to the specimen conveyance device 3 by the sending mechanism. The controller of the specimen inserting device 2 is communicably connected to the system control device 8 by way of the LAN, wherein a number is assigned to the sample rack when the sample rack is detected by the sensor, and the assigned number is transmitted to the system control device 8 when sending the sample rack to the specimen conveyance device 3.

Figure 2:
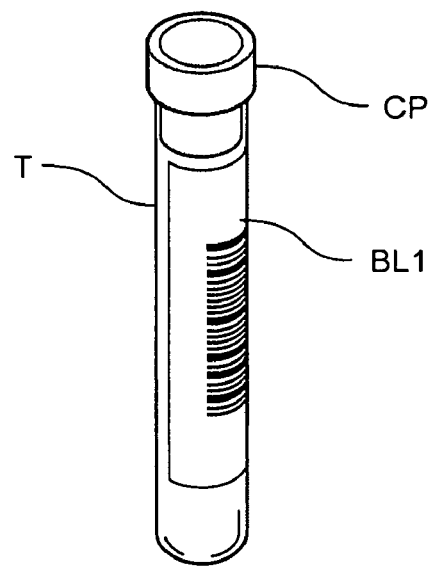
FIG. 2 is a perspective view showing an outer appearance of a specimen container.
Figure 3:
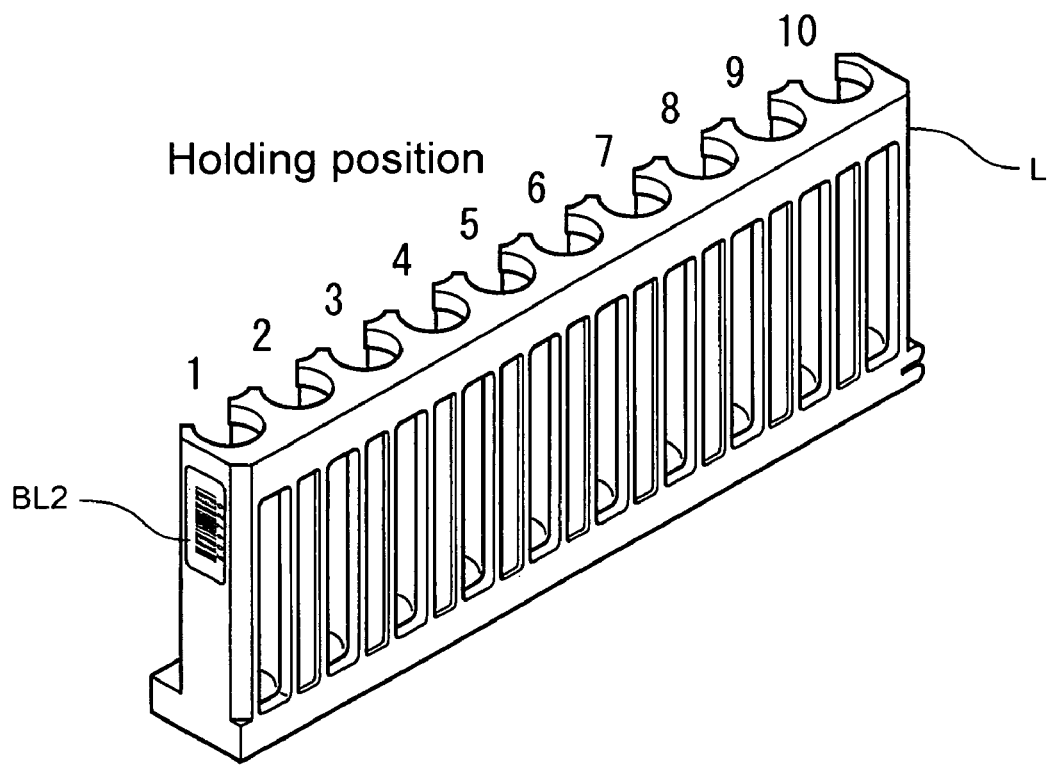
FIG. 3 is a perspective view showing an outer appearance of a sample rack.

FIG. 2 is a perspective view showing an outer appearance of the specimen container, and FIG. 3 is a perspective view showing an outer appearance of a sample rack. As shown in FIG. 2, the specimen container T has a tubular shape, and the upper end is opened. The blood specimen collected from a patient is accommodated therein, and the opening at the upper end is sealed by a lid CP. The specimen container T is made of glass or synthetic resin having translucency, so that the blood specimen inside can be seen. A barcode label BL1 is attached to the side surface of the specimen container T. A barcode indicating a specimen ID is printed on the barcode label BL1. The sample rack L can hold ten specimen containers T side by side. Each specimen container T is held in a perpendicular state (standing state) in the sample rack L. A barcode label BL2 is attached to the side surface of the sample rack L. A barcode indicating a rack ID is printed on the barcode label BL2.

<Configuration of Specimen Conveyance Device 3>

The configuration of the specimen conveyance device 3 will now be described. As shown in FIG. 1, the specimen processing system includes three specimen conveyance devices 3. The specimen conveyance devices 3, 3, 3 are arranged on the front side of the three measurement units 51, 51, 51 of the blood cell analyzer 5. The adjacent specimen conveyance devices 3, 3 are connected, so that the sample rack L (shown in FIGS. 3 and 4-5) can be sent or received. The specimen conveyance device 3 on the rightmost side is connected to the specimen inserting device 2 described above so that the sample rack L conveyed out from the specimen inserting device 2 can be introduced. The specimen conveyance device 3 on the leftmost side is connected to the specimen conveyance device 301 so that the sample rack L can be conveyed out to the specimen conveyance device 301.

Figure 4:
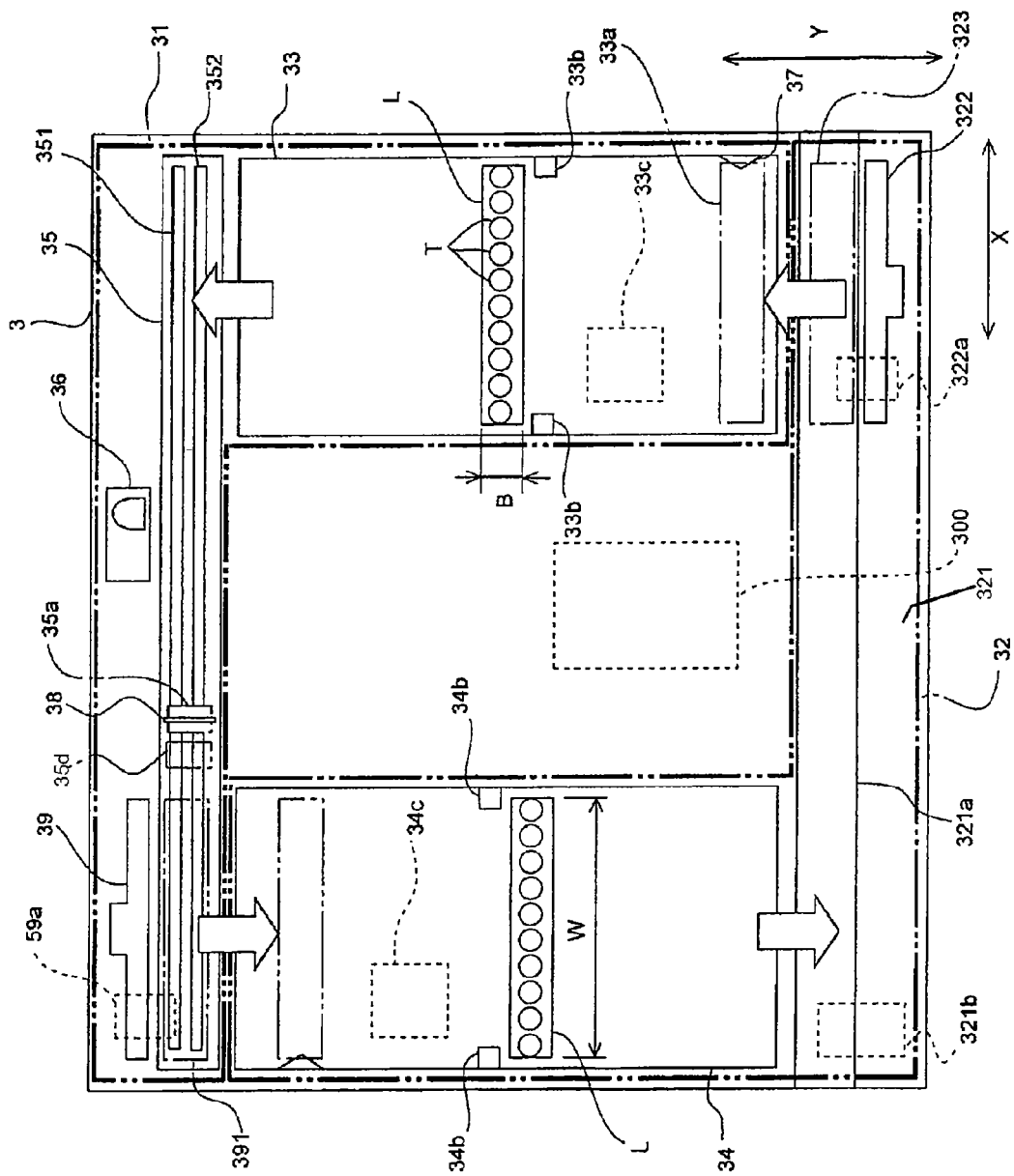
FIG. 4 is a plan view showing a configuration of a specimen conveyance device according to the embodiment.

FIG. 4 is a plan view showing a configuration of the specimen conveyance device 3. As shown in FIG. 4, the specimen conveyance device 3 includes a first conveyance mechanism 31 for supplying the specimen to a measurement unit 51 (shown in FIG. 1) of the blood cell analyzer 5 (shown in FIG. 1), a second conveyance mechanism 32 for conveying the specimen to the specimen conveyance device 3 (or specimen conveyance device 310) on the downstream side, and a controller 300 for controlling the second conveyance mechanism. The first conveyance mechanism 31 includes a pre-analysis rack holder 33 capable of temporarily holding a plurality of sample racks L for holding the specimen container T accommodating the specimen not being analyzed, a rack conveyance portion 35 for horizontally and linearly moving the sample rack L in the direction of the arrow X in the figure, a barcode readout portion 36 for reading out the rack barcode, a rack sensor 37 for detecting the presence of the sample rack L, a specimen container sensor 38 for detecting the presence of the specimen container T, and a rack sending portion 39 for sending the sample rack L to the second conveyance mechanism 32.

The pre-analysis rack holder 33 has a square shape in plan view, which width is slightly larger than the width of the sample rack L. The pre-analysis rack holder 33 is formed to be one step lower than the peripheral surface so that the sample rack L not being analyzed is mounted on the upper surface. The pre-analysis rack holder 33 is connected to the second conveyance mechanism 32, so that the sample rack L is sent from the second conveyance mechanism 32 by the rack sending portion 322 of the second conveyance mechanism 32, to be hereinafter described. The rack sensor 37 is attached near the pre-analysis rack holder 33, and a rack detection position 33a where the sample rack L is detected by the rack sensor 37 is arranged on the pre-analysis rack holder 33. The sample rack L sent from the second conveyance mechanism 32 is positioned at the rack detection position 33a, so that the relevant sample rack L is detected by the rack sensor 37. A rack sending portion 33b is arranged towards the inner side in a projecting manner from both side surfaces of the pre-analysis rack holder 33. When the sample rack L is detected by the rack sensor 37, it engages with the sample rack L by the projection of the rack sending portion 33b, and the sample rack L is moved to the back side when moved to the back side in such state (direction of approaching the rack conveyance portion 35). Such rack sending portion 33b is configured to be drivable by a stepping motor 33c arranged on the lower side of the pre-analysis rack holder 33.

As shown in FIG. 4, the rack conveyance portion 35 can move the sample rack L moved by the pre-analysis rack holder 33 in the X direction. A specimen container detection position 35a where the specimen container is detected by the specimen container sensor 38, and a specimen supply position 35c where the specimen is supplied to the measurement unit 51 (shown in FIG. 1) of the blood cell analyzer 5 (shown in FIG. 1) are provided on a conveyance path of the sample rack L by the rack conveyance portion 35. The rack conveyance portion 35 is configured to convey the sample rack L such that the specimen is conveyed to the specimen supply position 35c through the specimen container detection position 35a. The specimen supply position 35d is a position on the downstream side in the conveyance direction by one specimen from the specimen container detection position 35a, wherein when the specimen is conveyed to the specimen supply position 35d by the rack conveyance portion 35, a hand portion of the measurement unit 51 of the blood cell analyzer 5, to be hereinafter described, grips the specimen container T of the relevant specimen, and the specimen container T is taken out from the sample rack L, and the specimen is aspirated from the specimen container T, so that the specimen is supplied to the measurement unit 51. After conveying the specimen container to the specimen supply position 35d, the rack conveyance portion 35 waits for the conveyance of the sample rack L while the supply of the specimen is completed and the specimen container T is returned to the sample rack L.

Figure 5:
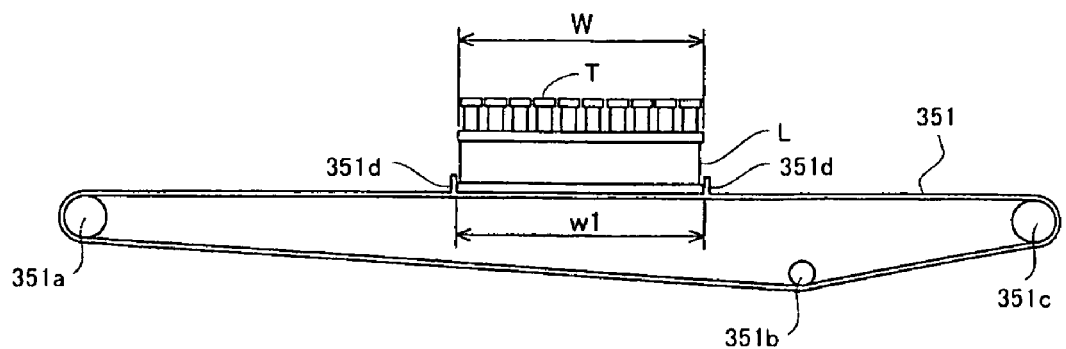
FIG. 5 is a front view showing a configuration of a first belt of a first conveyance mechanism.
Figure 6:
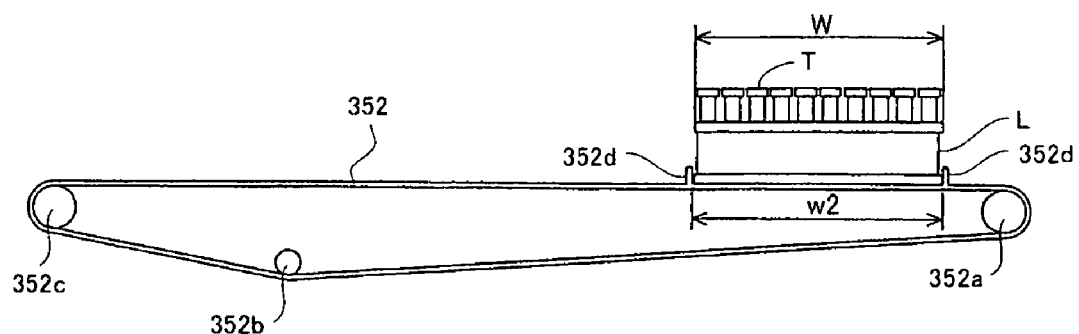
FIG. 6 is a front view showing a configuration of a second belt of the first conveyance mechanism.

The rack conveyance portion 35 includes two belts, first belt 351 and a second belt 352, that are independently operable. The widths b1 and b2 in the direction of the arrow Y of the first belt 351 and the second belt 352 are the size of smaller than or equal to half of the width B in the direction of the arrow Y of the sample rack L. Such first belt 351 and second belt 352 are arranged in parallel so as not to run out from the width B of the sample rack L when the rack conveyance portion 35 conveys the sample rack L. FIG. 5 is a front view showing a configuration of the first belt 351, and FIG. 6 is a front view showing a configuration of the second belt 352. As shown in FIGS. 5 and 6, the first belt 351 and the second belt 352 are respectively formed to an annular shape, wherein the first belt 351 is arranged to surround rollers 351a to 351c, and the second belt 352 is arranged to surround rollers 352a to 352c. Two projecting pieces 351d having an inner width w1 slightly (e.g., 1 mm) larger than the width W in the X direction of the sample rack L are arranged on the outer peripheral part of the first belt 351, and similarly, two projecting pieces 352d having an inner width w2 of the same extent as the inner width w1 are arranged on the outer peripheral part of the second belt 352. The first belt 351 is configured to move the sample rack L in the direction of the arrow X by being moved at the outer periphery of the rollers 351a to 351c by the stepping motor 351e while holding the sample rack L on the inner side of the two projecting pieces 351d. The second belt 352 is configured to move the sample rack L in the direction of the arrow X by being moved at the outer periphery of the rollers 352a to 352c by the stepping motor 352e while holding the sample rack L on the inner side of the two projecting pieces 352d. The first belt 351 and the second belt 352 are also configured to move the sample rack L independent from each other.

The barcode readout portion 36 reads the specimen barcode of the specimen container T shown in FIGS. 2 and 3, and also reads the rack barcode attached to the sample rack L. The relevant barcode readout portion 36 is configured to read the specimen barcode of the specimen container T while horizontally rotating the target specimen container T, while being accommodated in the sample rack L, by a rotation device (not shown). Thus, even if the barcode label BL1 of the specimen container T is positioned on the opposite side with respect to the barcode readout portion 36, the barcode label BL1 can face the barcode readout portion 36 by rotating the specimen container T, and the specimen barcode can be read by the barcode readout portion 36. The rack barcode of the sample rack L is recorded with the rack ID uniquely given to each sample rack L, and is used to manage the analysis result of the specimen, and the like.

The rack sensor 37 and the specimen container sensor 38 are contact-type sensors, and respectively include a curtain-shaped contact piece, a light emitting element for emitting light, and a light receiving element (not shown). In the rack sensor 37 and the specimen container sensor 38, the contact piece is bent by contacting the detected object of the detection target, and as a result, the light emitted from the light emitting element is reflected by the contact piece and received by the light receiving element. Therefore, when the specimen container T of the detection target accommodated in the sample rack L passes below the specimen container sensor 38, the contact piece is bent by the specimen container T, and the specimen container T is detected.

The rack sending portion 39 is arranged to face the post-analysis rack holder 34, to be hereinafter described, with the rack conveyance portion 35 in between, and is configured to horizontally linearly move in the direction of the arrow Y by the driving force of the stepping motor 59a. Thus, when the sample rack L is conveyed to a position 391 (hereinafter referred to as "post-analysis rack sending position") between the post-analysis rack holder 34 and the rack sending portion 39, the rack sending portion 39 is moved to the post-analysis rack holder 34 side so that the sample rack L can be pushed and moved into the post-analysis rack holder 34. The sample rack L, which analysis is completed, is sent from the first conveyance mechanism 31 to the second conveyance mechanism 32 in such manner.

The second conveyance mechanism 32 includes a rack conveyance portion 321, a rack sending portion 322, and the post-analysis rack holder 34. The rack conveyance portion 321 extends in the direction of the arrow X in the figure, and can horizontally linearly move the sample rack L in the direction of the arrow X. Such rack conveyance portion 321 includes an annular belt 321a and a stepping motor 321b, wherein the belt 321a rotates in the direction of the arrow X by the driving force of the stepping motor 321b. The sample rack L mounted on the belt 321a is thereby movable in the X direction. The rack sending portion 322 is arranged to face the pre-analysis rack holder 321 with the rack conveyance portion 321 in between on the front side of the pre-analysis rack holder 33, and is configured to horizontally and linearly move in the direction of the arrow Y by the driving force of the stepping motor 322a. Thus, when the sample rack L is conveyed to a position 323 (hereinafter referred to as "pre-analysis rack sending position") between the pre-analysis rack holder 33 and the rack sending portion 322, the rack sending portion 322 is moved to the pre-analysis rack holder 33 side so that that sample rack L is pushed and moved to the rack detection position 33a in the pre-analysis rack holder 33.

The post-analysis rack holder 34 has a square shape in plane view, which width is slightly larger than the width of the sample rack L. The post-analysis rack holder 34 is formed to be one step lower than the peripheral surface so that the sample rack L, which analysis is completed, is mounted on the upper surface thereof. The post-analysis rack holder 34 is connected to the rack conveyance portion 35, so that the sample rack L is sent from the rack conveyance portion 35 by the rack sending portion 39. A rack sending portion 34b is arranged towards the inner side in a projecting manner from both side surfaces of the post-analysis rack holder 34. When the sample rack L is conveyed in by the rack sending portion 39, it engages with the sample rack L by the projection of the rack sending portion 34b, and the sample rack L is moved to the front side when moved to the front side in such state (direction of approaching the rack conveyance portion 321). Such rack sending portion 34b is configured to be drivable by the stepping motor 34c arranged on the lower side of the post-analysis rack holder 34.

The second conveyance mechanism 32 having such configuration is controlled by the controller 300. The first conveyance mechanism 31 is controlled by the information processing unit 52 of the blood cell analyzer 5, to be hereinafter described. The controller 300 is configured by CPU, ROM, RAM, and the like (not shown), and the CPU can execute the control program of the second conveyance mechanism 32 stored in the ROM. The controller 300 has an Ethernet (registered trademark) interface so as to be communicably connected to the information processing unit 52 and the system control device 8 through the LAN.

According to such configuration, the specimen conveyance device 3 conveys the sample rack L conveyed from the specimen inserting device 2 to the pre-analysis rack sending position 323 by the second conveyance mechanism 32, moves the same to the pre-analysis rack holder 33 of the first conveyance mechanism by the rack sending portion 322, sends the sample rack L from the pre-analysis rack holder 33 to the rack conveyance portion 35, and conveys the same by the rack conveyance portion 35, so that the specimen can be supplied to the measurement unit 51 of the blood cell analyzer 5. The sample rack L accommodating the specimen, which aspiration is completed, is moved to the post-analysis rack sending position 391 by the rack conveyance portion 35, and sent to the post-analysis rack holder 34 by the rack sending portion 39. The sample rack L held by the post-analysis rack holder 34 is moved to the rack conveyance portion 321 of the second conveyance mechanism 32, and conveyed out to the device of the post-stage (specimen conveyance device 3 or 301) by the rack conveyance portion 321. If the sample rack L accommodating the specimen to be processed in the measurement unit 51 or the smear producing device 6 at the downstream side in conveyance or the specimen, which analysis is completed, is accepted by the specimen conveyance device 3 from the device of the pre-stage, the sample rack L is conveyed out in the direction of the arrow X by the rack conveyance portion 321 of the second conveyance mechanism 32, and conveyed out as it is to the specimen conveyance device 3 of the post-stage.

<Configuration of Specimen Conveyance Device 301>

As shown in FIG. 1, the specimen conveyance device 301 is arranged on the front side of the smear producing device 6. The specimen conveyance device 301 is connected, at the right side end, to the specimen conveyance device 3 positioned at the most downstream side in conveyance (left side in the figure) of the three specimen conveyance devices 3, 3, 3, and is connected, at the left side end, to the specimen accommodating device 4.

The specimen conveyance device 301 includes a conveyor 302 and a rack slider 303. The conveyor 302 is arranged with two rack conveyance paths 302a, 302b respectively extending in the left and right direction. The rack conveyance path 302a proximate to the smear producing device 6 is the measurement line for conveying the sample rack L accommodating the specimen to be supplied to the smear producing device 6. The rack conveyance path 302b distant from the smear producing device 6 is the skip line for conveying the sample rack L not accommodating the specimen to be supplied to the smear producing device 6. The conveyor 302 includes a CPU and a memory, and includes a controller (not shown) for controlling each operation mechanism.

The rack slider 303 is arranged on the right side of the conveyor 302, and allocates and inserts the sample rack L to the measurement line 302a and the skip line 302b of the conveyor 302.

<Configuration of Specimen Accommodating Device 4>

The specimen accommodating device 4 is configured so that a plurality of sample racks L can be mounted. The relevant specimen accommodating device 4 receives the sample rack L, which is terminated with analysis and smear production, from the specimen conveyance device 301, and accommodates the same.

<Configuration of Blood Cell Analyzer 5>

The blood cell analyzer 5 is a multi-item blood cell analyzer of optical flow cytometry manner, and acquires the lateral scattered light intensity, the fluorescence intensity, and the like related to the blood cell contained in the blood specimen, classifies the blood cell contained in the specimen based on the same, counts the number of blood cells for every type, creates a scattergram in which the classified blood cells are colored by type, and displays the same. The blood cell analyzer 5 includes the measurement unit 51 for measuring the blood specimen, and the information processing unit 52 for processing the measurement data output from the measurement unit 51 and displaying the analysis result of the blood specimen.

As shown in FIG. 1, the blood analyzer 5 includes three measurement units 51, 51, 51 and one information processing unit 52. The information processing unit 52 is communicably connected to the three measurement units 51, 51, 51 and the three specimen conveyance devices 3, 3, 3, and can control the operation of the three measurement units 51, 51, 51, and the three first conveyance mechanisms 31, 31, 31.

Figure 7:
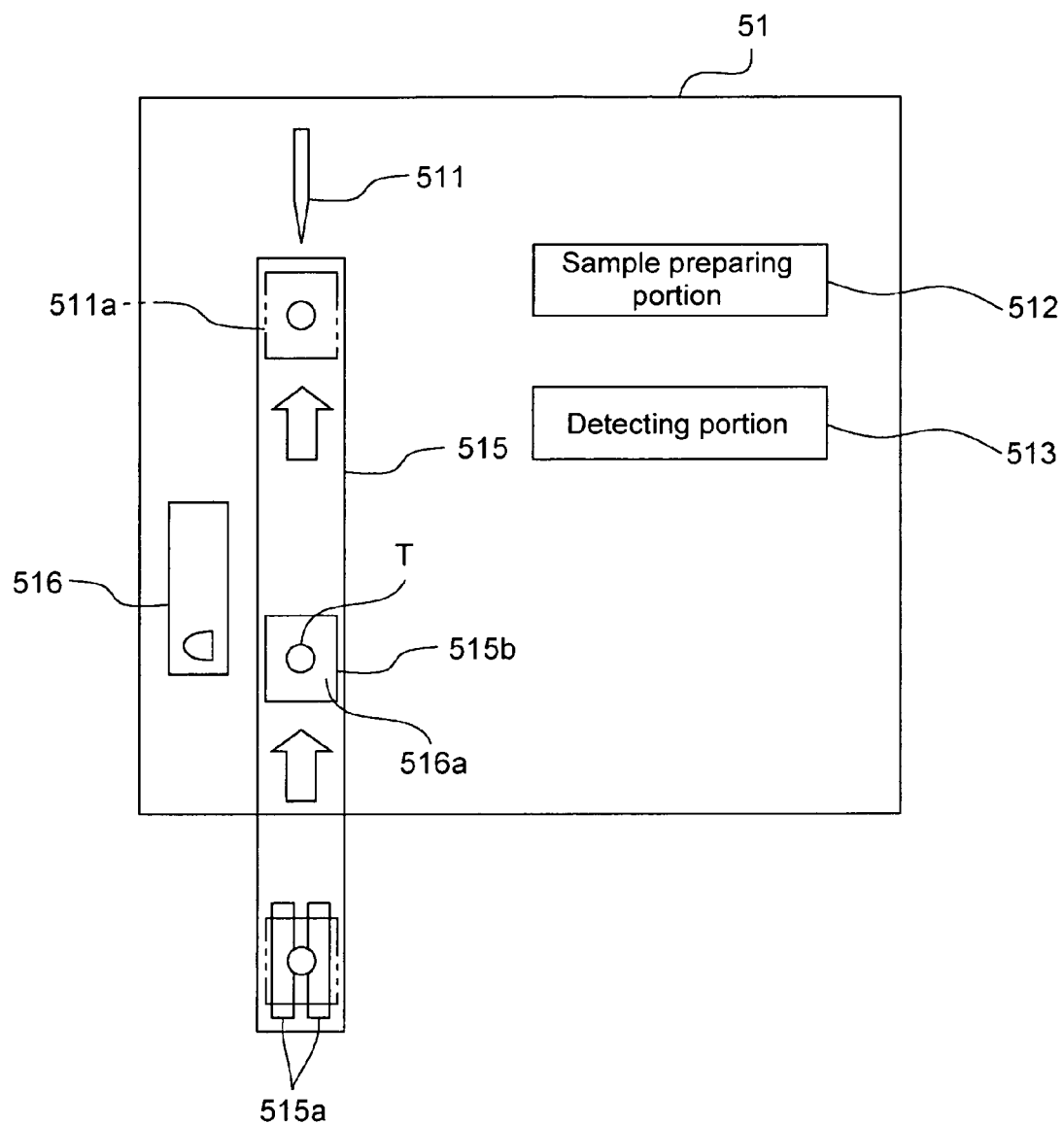
FIG. 7 is a block diagram showing a configuration of a measurement unit of a blood cell analyzer according to the embodiment.

The three measurement units 51, 51, 51 have the same configuration. FIG. 7 is a block diagram showing a configuration of the measurement unit 51. As shown in FIG. 7, the measurement unit 51 includes a specimen aspirating portion 511 for aspirating the blood or the specimen from the specimen container (blood collecting tube) T, a sample preparing portion 512 for preparing a measurement sample used in the measurement from the blood aspirated by the specimen aspirating portion 511, and a detecting portion 513 for detecting the blood cell from the measurement sample prepared by the sample preparing portion 512. The measurement unit 51 further includes a take-in port (not shown) for taking in the specimen container T accommodated in the sample rack L conveyed by the rack conveyance portion 35 of the specimen conveyance device 3 into the measurement unit 51, and a specimen container conveyance portion 515 for taking in the specimen container T from the sample rack L into the measurement unit 51 and conveying the specimen container T to the aspirating position by the specimen aspirating portion 511.

An aspirating tube (not shown) is arranged at the distal end of the specimen aspirating portion 511. The specimen aspirating portion 511 is movable in the vertical direction, and is moved to the lower side so that the aspirating tube passes through the lid CP of the specimen container T conveyed to the aspirating position to aspirate the blood inside.

The detecting portion 513 is configured to perform the RBC (Red Blood Cell) detection and the PLT (Platelet) detection through the sheath flow DC detection method, and to perform the HGB (Hemoglobin) detection through the SLS-hemoglobin method. The detecting portion 513 is configured to perform the WBC (White Blood Cell) detection through the flow cytometry method using the semiconductor laser.

The specimen container conveyance portion 515 includes a hand portion 515a capable of gripping the specimen container T. The hand portion 515a includes a pair of gripping members arranged facing each other, and can approach or separate the gripping members to and from each other. The specimen container T can be gripped by approaching the relevant gripping members with the specimen container T in between. The specimen container conveyance portion 515 can move the hand portion 515a in the up and down direction and in the front and back direction (Y direction), and can oscillate the hand portion 515a. Thus, the specimen container T accommodated in the sample rack L and positioned at the supply position 35c can be gripped by the hand portion 515a, the specimen container T can be taken out from the sample rack L by moving the hand portion 515a upward in the relevant state, and the specimen in the specimen container T can be stirred by oscillating the hand portion 515a.

The specimen container conveyance portion 515 includes a specimen container setting portion 515b with a hole for receiving the specimen container T. The specimen container T gripped by the hand portion 515a described above is moved after stirring is completed, and the gripped specimen container T is inserted to the hole of the specimen container setting portion 515b. Thereafter, the specimen container T is released from the hand portion 515b by separating the gripping members, and the specimen container T is set in the specimen container setting portion 515b. The relevant specimen container setting portion 515b is horizontally movable in the Y direction by the power of the stepping motor (not shown). A barcode readout portion 516 is arranged inside the measurement unit 51. The specimen container setting portion 515b is movable to the barcode reading position 516a near the barcode readout portion 516 and the aspirating position 511a by the specimen aspirating portion 511. When the specimen container setting portion 515b is moved to the barcode reading position 516a, the set specimen container T is horizontally rotated by a rotation mechanism (not shown), and the specimen barcode is read by the barcode readout portion 516. Thus, even if the barcode label BL1 of the specimen container T is positioned on the opposite side with respect to the barcode readout portion 516, the barcode label BL1 can be directed towards the barcode readout portion 516 by rotating the specimen container T so that the specimen barcode can be read by the barcode readout portion 516. When the specimen container setting portion 515b is moved to the aspirating position, the specimen is aspirated from the set specimen container T by the specimen aspirating portion 511.

Figure 8:
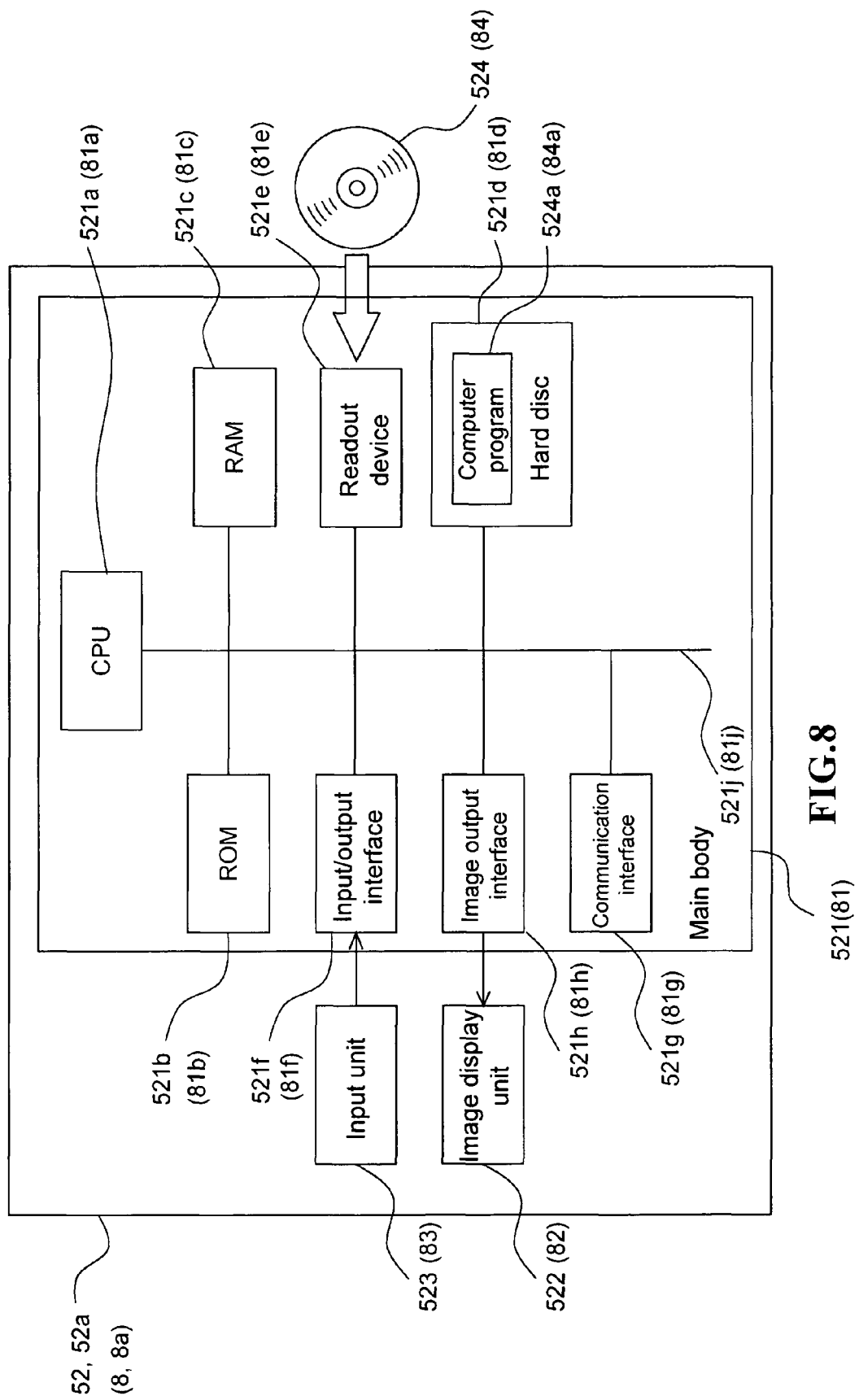
FIG. 8 is a block diagram showing a configuration of an information processing unit of the blood cell analyzer according to the embodiment.

The configuration of the information processing unit 52 will now be described. The information processing unit 52 is configured by a computer. FIG. 8 is a block diagram showing a configuration of the information processing unit 52. The information processing unit 52 is realized by a computer 52a. As shown in FIG. 8, the computer 52a includes a main body 521, an image display unit 522, and an input unit 523. The main body 521 includes a CPU 521a, a ROM 521b, a RAM 521c, a hard disc 521d, a readout device 521e, an input/output interface 521f, a communication interface 521g, and an image output interface 521h, wherein the CPU 521a, the ROM 521b, the RAM 521c, the hard disc 521d, the readout device 521e, the input/output interface 521f, the communication interface 521g, and the image output interface 521h are connected by a bus 521j.

The CPU 521a can execute the computer program loaded in the RAM 521c. The computer 52a functions as the information processing unit 52 by causing the CPU 521a to execute the computer program 524a for the specimen analysis and for the control of the measurement unit 51 and the first conveyance mechanism 31, to be hereinafter described.

The ROM 521b is configured by mask ROM, PROM, EPROM, EEPROM, and the like, and is recorded with the computer program executed by the CPU 521a, the data used when executing the computer program, and the like.

The RAM 521c is configured by SRAM, DRAM, or the like. The RAM 521c is used to read out the computer program 524a recorded in the hard disc 521d. The RAM 521c is used as a work region of the CPU 521a when the CPU 521a executing such computer programs.

The hard disc 521d is installed with various computer programs to be executed by the CPU 521a, and the data used for the execution of the computer program such as an operating system and an application program. The computer program 524a to be hereinafter described is also installed in the hard disc 521d.

The readout device 521e is configured by flexible disc drive, CD-ROM drive, DVD-ROM, or the like. The readout device 521e can read out computer program or data recorded in a portable recording medium 524. The portable recording medium 524 stores the application program 524a for causing the computer to function as the information processing unit 52, wherein the computer 52a reads out the computer program 524a from the portable recording medium 524, and installs the computer program 524a in the hard disc 521d.

The computer program 524a is not limited to being provided by the portable recording medium 524, and may be provided through an electrical communication line from an external device communicably connected to the computer 52a by the electrical communication line (wired or wireless). For instance, the computer program 524a may be stored in a hard disc of a server computer on the Internet, and the computer 52a may access the server computer, download the computer program, and install the same in the hard disc 521d.

The hard disc 521d is installed with a multi-task operating system such as Windows (registered trademark) manufactured and sold by US Microsoft Co. In the following description, the computer program 524a according to the present embodiment operates on the operating system.

The input/output interface 521f is configured by serial interface such as USB, IEEE1394, RS-232C; parallel interface such as SCSI, IDE, IEEE1284; analog interface including D/A converter, A/D converter and the like. The input/output interface 521$f$ is connected with the input unit 523 such as a keyboard and a mouse, and the user can input data to the computer 52$a$ by using the input unit 523. The input/output interface 521$f$ is connected to three measurement units 51, 51, 51. The data can be transmitted and received with each of the three measurement units 51, 51, 51.

The communication interface 521$g$ is an Ethernet (registered trademark) interface. The communication interface 521$g$ is connected to the system control device 8 through the LAN. The computer 52$a$ can transmit and receive data with the system control device 8 connected to the LAN using a predetermined communication protocol by the communication interface 521$g$. The communication interface 521$g$ is communicably connected to the host computer 9 through the LAN.

The image output interface 521$h$ is connected to the image display unit 522 configured by LCD, CRT, or the like, and outputs a video signal corresponding to the image data provided from the CPU 521$a$ to the image display unit 522. The image display unit 522 displays an image (screen) according to the input video signal.

<Configuration of Smear Producing Device 6>

The smear producing device 6 aspirates the blood specimen, drops the blood specimen on a slide glass, thinly spreads the blood specimen on the slide glass, dries the blood specimen, and then supplies staining fluid to the slide glass to stain the blood on the slide glass to thereby produce the smear.

Figure 9:
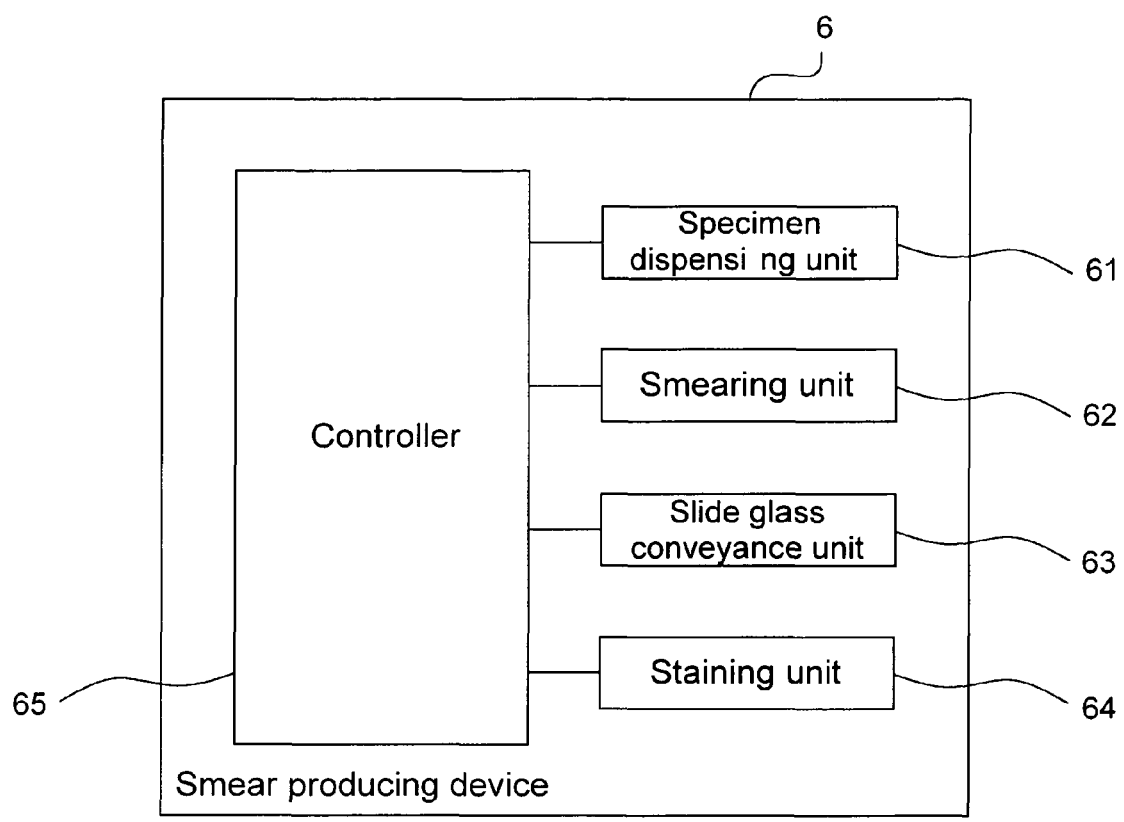
FIG. 9 is a block diagram showing a schematic configuration of a smear producing device according to the embodiment.

FIG. 9 is a block diagram showing a schematic configuration of the smear producing device 6. As shown in FIG. 9, the smear producing device 6 includes a specimen dispensing unit 61, a smearing unit 62, a slide glass conveyance unit 63, a staining unit 64, and a controller 65.

The specimen dispensing unit 61 includes an aspiration tube (not shown), which aspiration tube is pierced to the lid C of the specimen container T of the sample rack L conveyed on the measurement line 31$a$ of the specimen conveyance device 3 to aspirate the blood specimen from the specimen container T. The specimen dispensing unit 61 is configured to drop the aspirated blood specimen on the slide glass. The smearing unit 62 is configured to smear and dry the blood specimen dropped onto the slide glass, and to print on the slide glass.

The slide glass conveyance unit 63 is provided to accommodate the slide glass smeared with the blood specimen by the smearing unit 62 in the cassette (not shown) and further convey such cassette. The staining unit 64 supplies the staining fluid to the slide glass in the cassette conveyed to the staining position by the slide glass conveyance unit 63. The controller 65 controls the specimen dispensing unit 61, the smearing unit 62, the slide glass conveyance unit 63, and the staining unit 64 according to a sample producing instruction provided from the specimen conveyance device 3, and executes the smear producing operation. The smear produced in such manner is sent to the blood cell image display device 7.

<Configuration of System Control Device 8>

The system control device 8 is configured by a computer, and controls the entire specimen processing system. The system control device 8 accepts the number of the sample rack L (shown in FIGS. 3 and 4-5) from the specimen inserting device 2, and determines the conveyance destination of the sample rack L.

The system control device 8 is configured by a computer 8$a$. As shown in FIG. 8, the computer 8$a$ includes a main body 81, an image display unit 82, and an input unit 83. The main body 81 includes a CPU 81$a$, a ROM 81$b$, a RAM 81$c$, a hard disc 81$d$, a readout device 81$e$, an input/output interface 81$f$, a communication interface 81$g$, and an image output interface 81$h$, wherein the CPU 81$a$, the ROM 81$b$, the RAM 81$c$, the hard disc 81$d$, the readout device 81$e$, the input/output interface 81$f$, the communication interface 81$g$, and the image output interface 81$h$ are connected by a bus 81$j$.

The hard disc 81$d$ is installed with various computer programs to be executed by the CPU 81$a$, and the data used for the execution of the computer program such as an operating system and an application program. The system control program 84$a$ to be hereinafter described is also installed in the hard disc 81$d$.

The readout device 81$e$ is configured by flexible disc drive, CD-ROM drive, DVD-ROM, or the like, and can read out computer program or data recorded in a portable recording medium 84. The portable recording medium 84 stores the system control program 84$a$ for causing the computer to function as the system control device 8, wherein the computer 8$a$ reads out the system control program 84$a$ from the portable recording medium 84, and installs the system control program 84$a$ in the hard disc 81$d$.

The input/output interface 81$f$ is configured by serial interface such as USB, IEEE1394, RS-232C; parallel interface such as SCSI, IDE, IEEE1284; analog interface including D/A converter, A/D converter and the like. The input/output interface 81$f$ is connected with the input unit 83 such as a keyboard and a mouse, and the user can input data to the computer 52$a$ by using the input unit 83.

The communication interface 81$g$ is an Ethernet (registered trademark) interface. The communication interface 81$g$ is connected to the specimen inserting device 2, the specimen conveyance device 3, the specimen accommodating device 4, the information processing unit 52, and the host computer 9 through the LAN. The computer 8$a$ can transmit and receive data with each device connected to the LAN by using a predetermined communication protocol by the communication interface 81$g$.

Other configurations of the system control device 8 are similar to the configuration of the information processing unit 52, and thus the description thereof will be omitted.

<Configuration of Host Computer 9>

The host computer 9 is configured by a computer, and includes a CPU, a ROM, a RAM, a hard disc, a communication interface, and the like. The communication interface is connected to the LAN, and can communication with the system control device 8, the information processing unit 52 of the blood cell analyzer 5, the image processing unit 73 of the blood cell image display device 7, the specimen inserting device 2, the specimen conveyance device 3, and the specimen accommodating device 4. The hard disc is stored with measurement orders. When receiving request data of the measurement order including the specimen ID from another device, the measurement data corresponding to such specimen ID is read out from the hard disc, and transmitted to the device of the requesting source. The configuration of the host computer 9 is similar to the configuration of other computers described above, and thus the description thereof will be omitted.

The operation of the specimen processing system 1 according to the present embodiment will be described below.

<Operation of Specimen Inserting Device 2>

The user places the sample rack L (shown in FIGS. 3 and 4-5) accommodating the specimen container T on the specimen inserting device 2 (shown in FIG. 1), operates the operation panel (not shown) of the specimen inserting device 2, and gives an instruction to start the analysis to the specimen processing system. The controller of the specimen inserting device 2 accepts such instruction to start the analysis, and starts to move the sample rack L. After accepting the instruction to start the analysis, the sample rack L of the specimen inserting device 2 is detected by a sensor of the specimen inserting device 2. When the sample rack L is detected by the sensor, a number (hereinafter referred to as "rack sequential number") is assigned to the sample rack L by the controller of the specimen inserting device 2. The rack sequential number is assigned to each sample rack L in the order detected by the sensor. Thereafter, the sample rack L placed on the specimen inserting device 2 is moved on the specimen inserting device 2 until reaching the carry-out position for carrying out the sample rack L. The controller of the specimen inserting device 2 then transmits carry-out request data including the rack sequential number assigned to the sample rack L to the system control device 8. When receiving the carry-out instruction from the system control device 8, the specimen inserting device 2 then carries out the sample rack L to the adjacent specimen conveyance device 3, and transmits carry-out completion data to the system control device 8.

<Operation of System Control Device 8>

The operation of the system control device 8 will now be described. The system control device 8 receives the carry-out request data from the specimen inserting device 2, and determines the conveying destination of the sample rack L by using the rack sequential number contained in the carry-out request data. This operation will be specifically described below.

Figure 10:
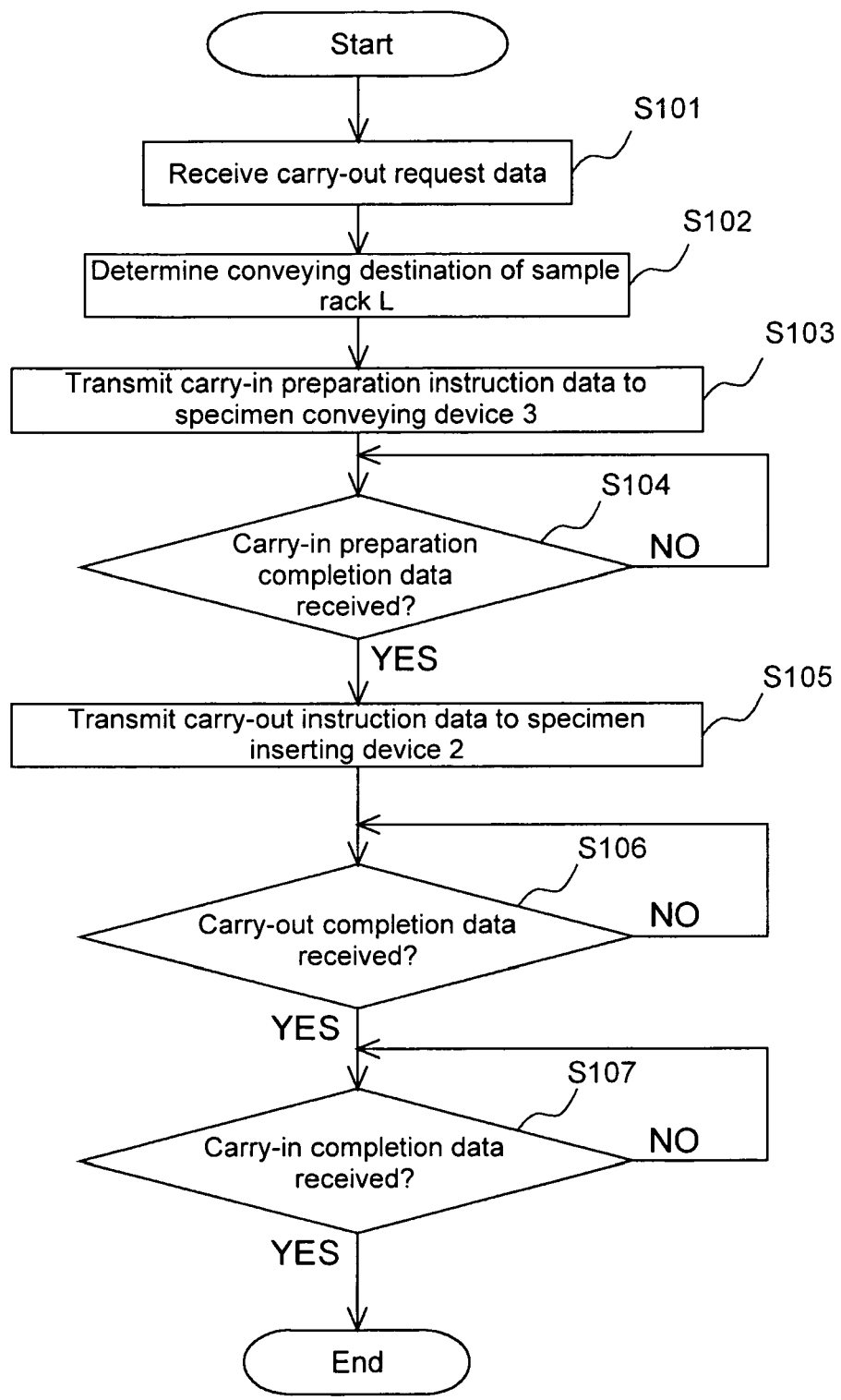
FIG. 10 is a flowchart showing a procedure of a conveying destination determination process of the system control device according to the embodiment.

FIG. 10 is a flowchart showing a procedure of a conveying destination determination process. The carry-out request data transmitted from the specimen inserting device 2 is received by the communication interface 81g of the system control device 8 (step S101). The system control program 84a executed by the CPU 81a of the system control device 8 is an event-driven program, wherein the process of step S102 is called out when the event of receiving the rack sequential number occurs in the CPU 81a.

In step S102, the CPU 81a determines the conveying destination of the sample rack L (shown in FIGS. 3 and 4-5) corresponding to the rack sequential number contained in the received carry-out request data. In the process, the system control device 8 (shown in FIG. 1) manages the state of each specimen conveyance device 3, 3, 3 (shown in FIGS. 1 and 4), and the conveying destination is determined by the state of the respective specimen conveyance device 3, 3, 3. For instance, at the beginning when the specimen processing system is activated, none of the measurement units 51, 51, 51 (shown in FIG. 1) is operating. Thus, the state of the first conveyance mechanisms 31, 31, 31 and the second conveyance mechanisms 32, 32, 32 of the specimen conveyance devices 3, 3, 3 connected to the measurement units 51, 51, 51 is "rack receivable". Therefore, in such case, one first conveyance mechanism 51 defined in advance is determined as the conveying destination. If the measurement of the specimen is executed by one measurement unit 51, the sample rack L exists on the first conveyance mechanism 31, and thus carrying out the sample rack L to the first conveyance mechanisms 31, 31 of the specimen conveyance devices 3, 3 connected to other measurement units 51, 51 is more efficient. Therefore, the first conveyance mechanism 31 not carrying out the sample rack L is determined as the conveying destination in such case.

The CPU 81a transmits carry-in preparation instruction data of the sample rack L based on the determined conveying destination to the specimen conveyance device 3 adjacent to the specimen inserting device 2 (i.e., specimen conveyance device 3 on the most right side in FIG. 1) (step S103). The carry-in preparation instruction data contains data (hereinafter referred to as "use conveyance line instruction data") indicating the conveyance line (first conveyance mechanism 31 or second conveyance mechanism 32) for conveying the sample rack L in such specimen conveyance device 3 and the rack sequential number of the sample rack L. That is, if the conveying destination of the sample rack L is the first conveyance mechanism 31 of the specimen conveyance device 3 adjacent to the specimen inserting device 2, data indicating the first conveyance mechanism is set as the use conveyance line instruction data in the carry-in preparation instruction data. If the first conveyance mechanism 31 of the specimen conveyance device 3 of the post-stage is determined as the conveying destination, data indicating the second conveyance mechanism is set as the use conveyance line instruction data in the carry-in preparation instruction data. As hereinafter described, the specimen conveyance device 3 receiving the carry-in preparation instruction data executes the preparation operation (operation enabling the reception of the sample rack L) of the conveyance mechanism indicated by the use conveyance line instruction data contained in the carry-in preparation instruction data, and then transmits the carry-in preparation completion data.

The CPU 81a waits for the carry-in preparation completion data from the specimen conveyance device 3 (NO in step S104). The carry-in preparation completion data is transmitted from the specimen conveyance device 3, wherein when the system control device 8 receives the carry-in preparation completion data (YES in step S104), the CPU 81a transmits the carry-out instruction data of the sample rack L to the specimen inserting device 2 (Step S105). As described above, when receiving the carry-out instruction data, the specimen inserting device 2 carries out the sample rack L to the specimen conveyance device 3 and transmits the carry-out completion data. The CPU 81a waits for the carry-out completion data from the specimen inserting device 2 (NO in step 106). The carry-out completion data is transmitted from the specimen inserting device 2, wherein when the system control device 8 receives the carry-out completion data (YES in step S106), the CPU 81a waists for the carry-in completion data from the specimen conveyance device 3 (NO in step S107). The carry-in completion data is transmitted from the specimen conveyance device 3, wherein when the system control device 8 receives the carry-in completion data (YES in step S107), the CPU 81a terminates the process.

Figure 11:
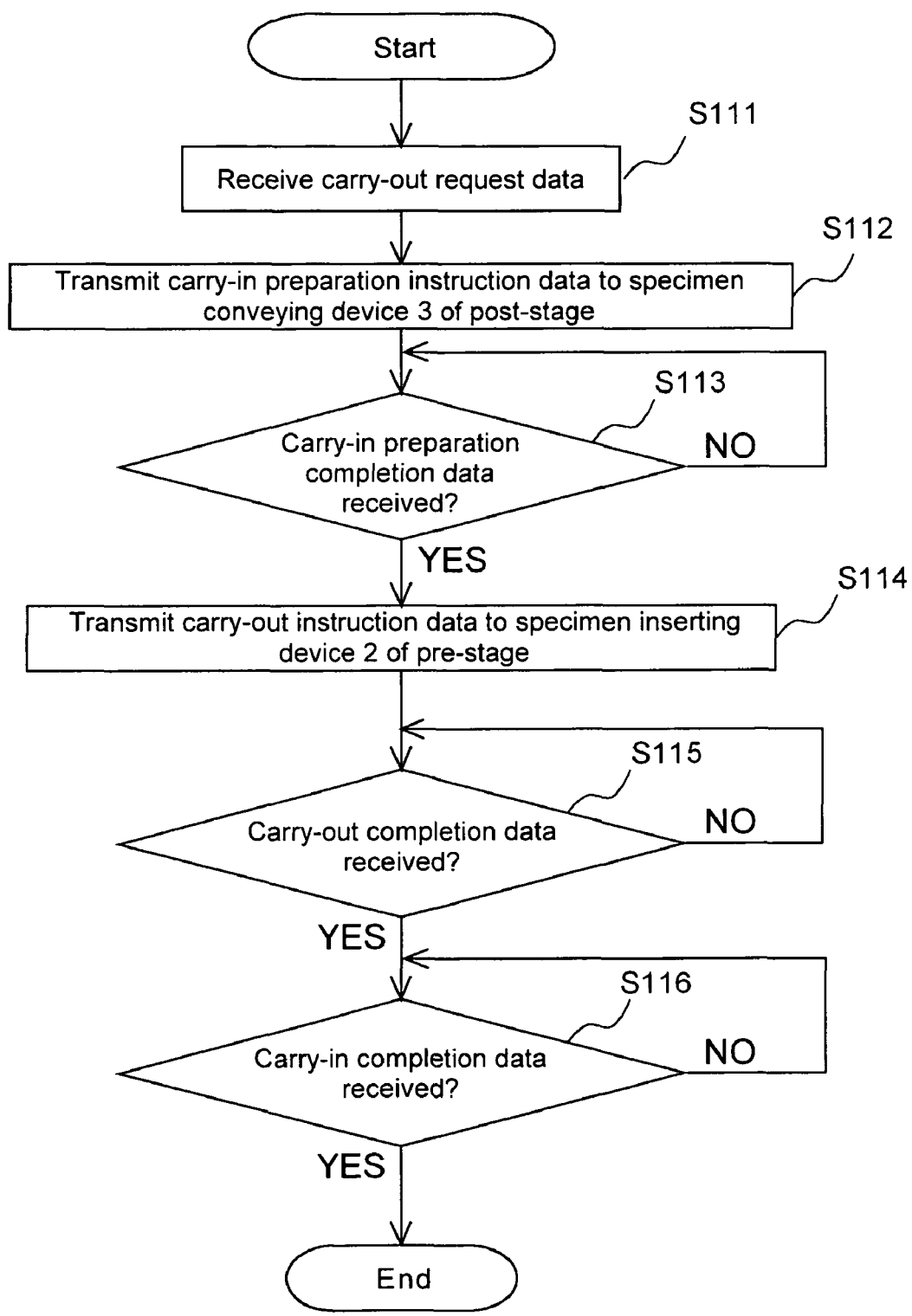
FIG. 11 is a flowchart indicating the procedure of a conveyance instruction process of the system control device according to the embodiment.

The conveyance instruction process of the system control device 8 will be described below. FIG. 11 is a flowchart indicating the procedure of the conveyance instruction process. As hereinafter described, the sample rack L is conveyed by the specimen conveyance device 3, wherein when the sample rack L reaches the terminating end position of the second conveyance mechanism 32, that is, the carry-out position for carrying out the sample rack L to the specimen conveyance device 3 (or specimen conveyance device 301) of the post-stage, the carry-out request data including the rack sequential number assigned to the sample rack L is transmitted from the specimen conveyance device 3. The carry-out request data transmitted from the specimen conveyance device 3 is received by the communication interface 81g of the system control device 8 (step S111). In the CPU 81a, the process of step S112 is called out when an event of receiving the carry-out request data from the specimen conveyance device 3 occurs.

In step S112, the CPU 81a transmits the carry-in preparation instruction data of the sample rack L based on the conveying destination determined in the conveying destination determination process to the specimen conveyance device 3 of the post-stage of the relevant specimen conveyance device 3 (step S112). The carry-in preparation instruction data is similar to the carry-in preparation instruction data described above, and thus the description thereof will be omitted.

The CPU 81a waits for the carry-in preparation completion data from the specimen conveyance device 3 (NO in step S113). The carry-in preparation completion data is transmitted from the specimen conveyance device 3, wherein when the system control device 8 receives the carry-in preparation completion data (YES in step S113), the CPU 81a transmits the carry-out instruction data of the sample rack L to the specimen conveyance device 3 of the pre-stage (carry-out side) (step S114). When receiving the carry-out instruction data, the specimen conveyance device 3 of the pre-stage carries out the sample rack L to the specimen conveyance device 3 of the post-stage, and transmits the carry-out completion data. The CPU 81a waits for the carry-out completion data from the specimen conveyance device 3 of the pre-stage (NO in step S115) and the carry-out completion data is transmitted from the specimen conveyance device 3 of the pre-stage, wherein when the system control device 8 receives the carry-out completion data (YES in step S115), the CPU 81a waits for the carry-in completion data from the specimen conveyance device 3 of the post-stage (NO in step S116). When the carry-in completion data is transmitted from the specimen conveyance device 3 of the post-stage, and the system control device 8 receives such as carry-in completion data (YES in step S116), the CPU 81a terminates the process.

<Operation of Controller 300 of Specimen Conveyance Device 3>

Figure 12:
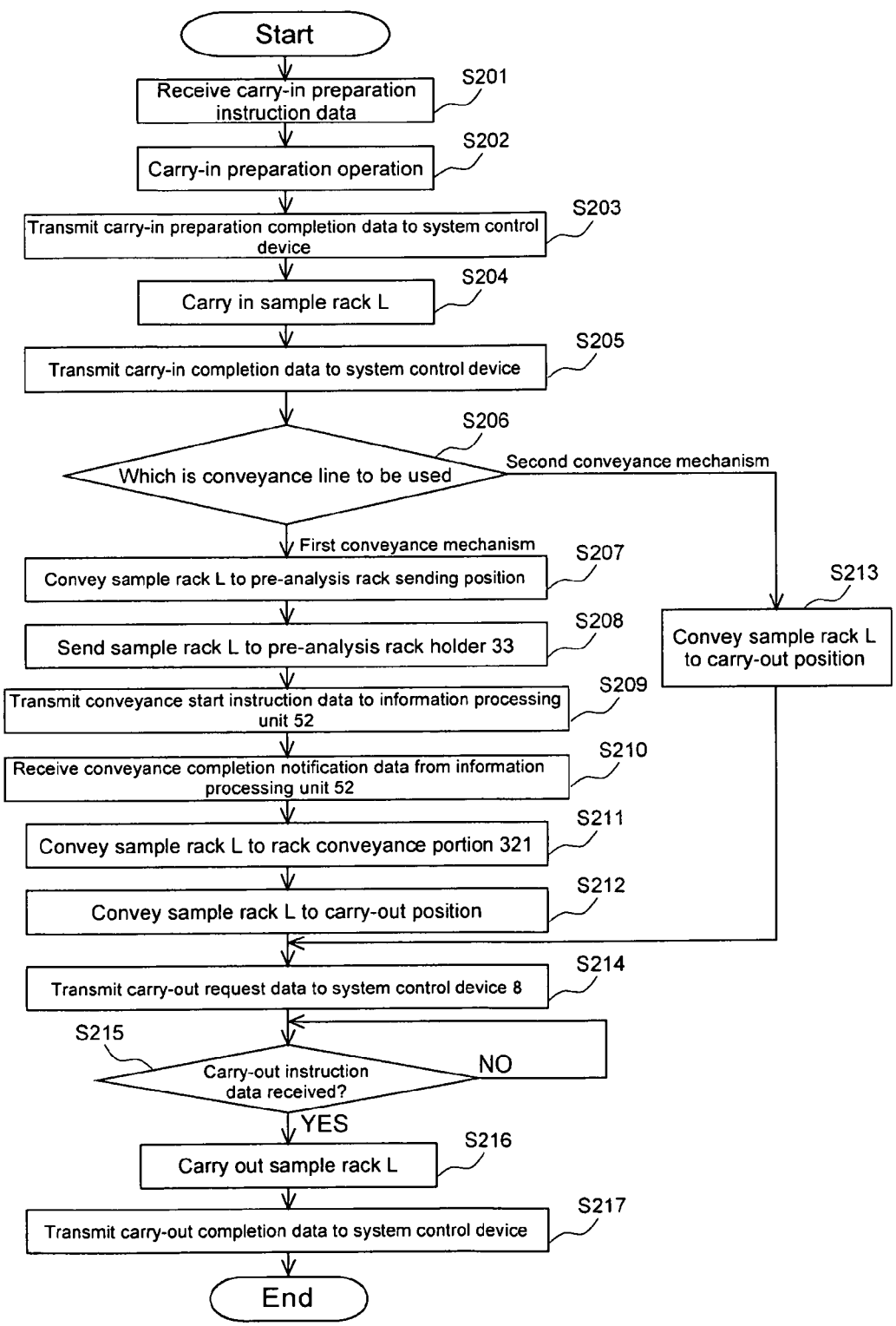
FIG. 12 is a flowchart showing a flow of control process of the second conveyance mechanism by the controller of the specimen conveyance device according to the embodiment.

The operation of the controller 300 of the specimen conveyance device 3 arranged on the front side of the blood cell analyzer 5 will be described. FIG. 12 is a flowchart showing a flow of control process of the second conveyance mechanism 32 by the controller 300. The carry-in preparation instruction data transmitted from the system control device 8 is received by the controller 300 (step S201). The conveyance control program executed by the CPU of the controller 300 is an event-driven program, wherein the process of step S202 is called out when the event of receiving the carry-in preparation instruction data occurs in the controller 300.

In step S202, the controller 300 drives the belt 321a of the second conveyance mechanism 32, for example, and thereby, executes the carry-in preparation operation (step S202). When the carry-in preparation is completed, the controller 300 transmits the carry-in preparation completion data for notifying that the carry-in preparation is completed to the system control device 8 (step S203).

The sample rack L is carried out from the device of the pre-stage according to the transmission of the carry-in preparation completion data, so that the sample rack L is carried in the second conveyance mechanism 32 (step S204). When the carrying in of the sample rack L is completed, the controller 300 transmits the carry-in completion data for notifying that the carry-in of the sample rack L is completed to the system control device 8 (step S205).

The controller 300 then determines which of the first conveyance mechanism 31 or the second conveyance mechanism 32 the use conveyance line instruction data contained in the carry-in preparation instruction data is indicating, that is, which of the first conveyance mechanism 31 or the second conveyance mechanism 32 is the conveyance line to be used (step S206). If the use conveyance line instruction data contained in the carry-in preparation instruction data indicates the first conveyance mechanism 31 in step S206, that is, if the first conveyance mechanism 31 is the conveyance line to be used ("first conveyance mechanism" in step S206), the controller 300 controls the rack conveyance portion 321 and conveys the sample rack L to the pre-analysis rack sending position (step S207), and thereafter drives the rack sending portion 322 to send the sample rack L to the pre-analysis rack holder 33 of the first conveyance mechanism 31 (step S208). Furthermore, the controller 300 transmits the conveyance start instruction data for instructing the start of conveyance of the sample rack L to the information processing unit 52 (step S209). The controller 300 may acquire the measurement data from the system controller 8 or the host computer 9, and transmit the acquired measurement data to the information processing unit 52 with the conveyance start instruction data.

Subsequently, the sample rack L is conveyed by the first conveyance mechanism 31 and the specimen is supplied to the measurement unit 51, as hereinafter described. After the measurement of all specimens held by the sample rack L is completed, the sample rack L is further conveyed by the first conveyance mechanism 31, and sent to the post-analysis rack holder 34. In this case, the conveyance completion notification data for notifying that the conveyance of the sample rack L by the first conveyance mechanism 31 is completed is transmitted from the information processing unit 52. The conveyance completion notification data transmitted from the information processing unit 52 is received by the controller 300 (step S210). In the CPU 521a, the process of step S211 is called out when an event of receiving the conveyance completion notification data occurs.

In step S211, the controller 300 drives the stepping motor 34c to operate the rack sending portion 34b, so that the sample rack L is moved to the rack conveyance portion 321 (step S211). The controller 300 then drives the stepping motor 321b to operate the rack conveyance portion 321, moves the sample rack L on the rack conveyance portion 321, and enables the sample rack L to reach the carry-out position for carrying out (step S212). Thereafter, the controller 300 advances the process to step S214.

If the use conveyance line instruction data contained in the carry-in preparation instruction data indicates the second conveyance mechanism 32 in step S206, that is, if the second conveyance mechanism 32 is the conveyance line to be used ("second conveyance mechanism" in step S206), the controller 300 controls the rack conveyance portion 321, moves the sample rack L on the rack conveyance portion 321, and enables the sample rack L to reach the carry-out position for carrying out (step S213). Thereafter, the controller 300 then advances the process to step S214.

In step S214, the controller 300 transmits the carry-out request data including the rack sequential number assigned to the sample rack L to the system control device 8 (step S214). The controller 300 then waits for the carry-out instruction data from the system control device 8 (NO in step S215), wherein when receiving the carry-out instruction data (YES in step S215), the controller 300 drives the stepping motor 321b to carry out the sample rack L to the adjacent specimen conveyance device 3 (step S216), and transmits the carry-out completion data to the system control device 8 (step S217). The controller 300 then terminates the process.

<Operation of Blood Cell Analyzer 5>

The operation of the blood cell analyzer 5 (shown in FIG. 1) will now be described. The information processing unit 52 (shown in FIG. 1) can set the conveyance control mode of either the first conveyance mode of performing the control of the first conveyance mechanism 31 in cooperation with the specimen conveyance device 3 (shown in FIG. 1), or the second conveyance control mode of performing the control of the first conveyance mechanism 31 in dependent from the specimen conveyance device 3. In the setting of the conveyance control mode, a setting screen for setting the conveyance control mode is displayed on the image display unit 522 of the information processing unit 52 (shown in FIG. 1), and either the first conveyance control mode or the second conveyance control mode is set when the user operates the input unit 523. When conveying the sample rack L (shown in FIGS. 3 and 4-5) with the entire specimen processing system, the first conveyance control mode is set. Here, the control operation of the first conveyance mechanism 31 of the information processing unit 52 in the first conveyance control mode will be described first.

Figure 13:
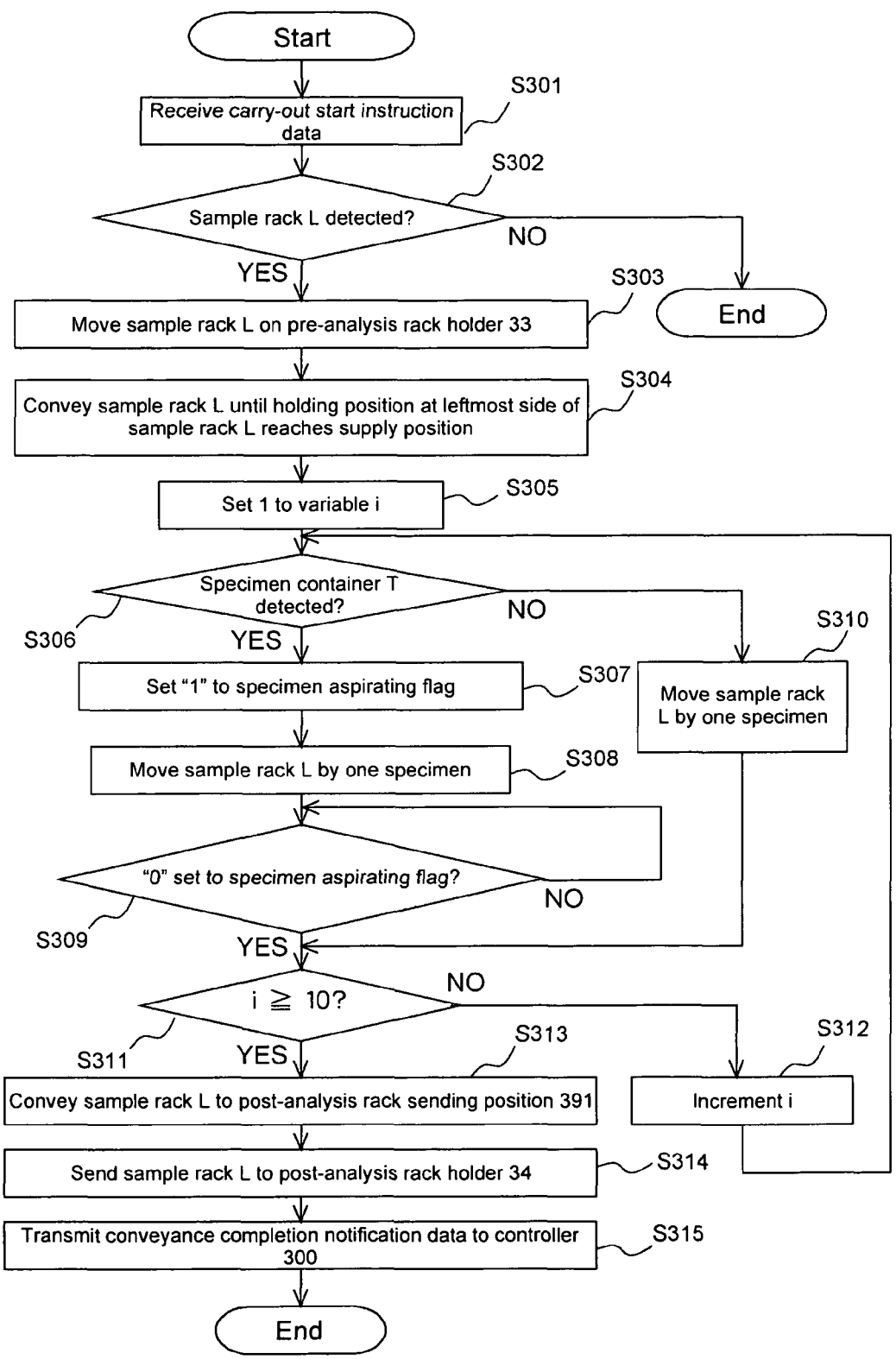
FIG. 13 is a flowchart showing a flow of the control process of the first conveyance mechanism in the first conveyance control mode by the information processing unit of the blood cell analyzer according to the embodiment.

FIG. 13 is a flowchart showing a flow of the control process of the first conveyance mechanism 31 in the first conveyance control mode by the information processing unit 52 of the blood cell analyzer 5. The conveyance start instruction data transmitted from the specimen conveyance device 3 is received by the communication interface 521g of the information processing unit 52 (step S301). The computer program 524a executed by the CPU 521a of the information processing unit 52 is an event-driven program, wherein the process of step S302 is called out when an event of receiving the conveyance start instruction data occurs in the CPU 521a.

When the sample rack L is sent to the rack detection position 33a of the pre-analysis rack holder 33 by the rack sending portion 322 as described above, the sample rack L is detected by the rack sensor 37. The CPU 521a determines whether or not the sample rack L is detected by the rack sensor 37 (step S302), and terminates the process if the sample rack L is not detected (NO in step S302). If the sample rack L is detected (YES in step S302), the CPU 521a operates the rack sending portion 33b by driving the stepping motor 33c, thereby moving the sample rack L on the pre-analysis rack holder 33 (step S303).

The CPU 521a drives the stepping motor 351e to operate the rack conveyance portion 35, thereby moving the sample rack L that reached the rack conveyance portion 35 until the holder positioned at the most left side in FIG. 1, of the holders of the specimen container T of the sample rack L, reaches the specimen container detection position (step S304). The CPU 521a then sets 1 to the variable i indicating the holding position of the specimen container T in the sample rack L (step S305), determines whether or not the specimen container T is detected at the specimen container detection position by the specimen container sensor 38 (step S306), sets "1" to the specimen aspirating flag arranged in the RAM 521c (step S307) if the specimen container T is detected (YES in step S306), and moves the sample rack L in the left direction by one specimen (step S308). The specimen container T detected by the specimen container sensor 38 is thereby positioned at the specimen supply position 35c, and the specimen is aspirated as hereinafter described. The initial value of the specimen aspirating flag is "0". The specimen aspirating flag is again set to "0" after the aspiration of the specimen is completed and the specimen container T is returned to the sample rack L by the hand potion 515a. The CPU 521a waits until the specimen aspirating flag is set to "0" (NO in step S309), and proceeds the process to step S311 if the specimen aspirating flag is set to "0" (YES in step S309).

If the specimen container T is not detected in step S306 (NO in step S306), the CPU 521a moves the sample rack L in the left direction by one specimen (step S310), and proceeds the process to step S311. In step S311, the CPU 521a determines whether or not i is greater than or equal to ten (step S311), wherein i is incremented by one (step S312) if i is smaller than ten (NO in step S311), and the process returns to step S306.

If i is greater than or equal to ten in step 5311 (YES in step S311), the CPU 521a drives the stepping motor 351e to operate the rack conveyance portion 35 thereby conveying the sample rack L to the post-analysis rack sending position 391 (step S313). The CPU 521a then drives the stepping motor 59a, operates the rack sending portion 39, sends the sample rack L to the post-analysis rack holder 34 (step S314), transmits the conveyance completion notification data for notifying that the conveyance of the sample rack L by the first conveyance mechanism 31 is completed to the specimen conveyance device 3 (step S315), and terminates the process. The specimen conveyance device 3 receiving the conveyance completion notification data conveys the sample rack L and carries out the sample rack L to the device of the post-stage, as described above.

The control operation of the first conveyance mechanism 31 of the information processing unit 52 in the second conveyance control mode will now be described. The second conveyance control mode is set the case where the second conveyance mechanism 32 cannot be operated and only the specimen analyzer 5 and the first conveyance mechanism 31 are to be operated such as the case where failure or abnormality occurs in the controller 300 or the second conveyance mechanism 32 of the specimen conveyance device 3 or the system control device 8, or the case where the system control device 8 is not activating.

Figure 14:
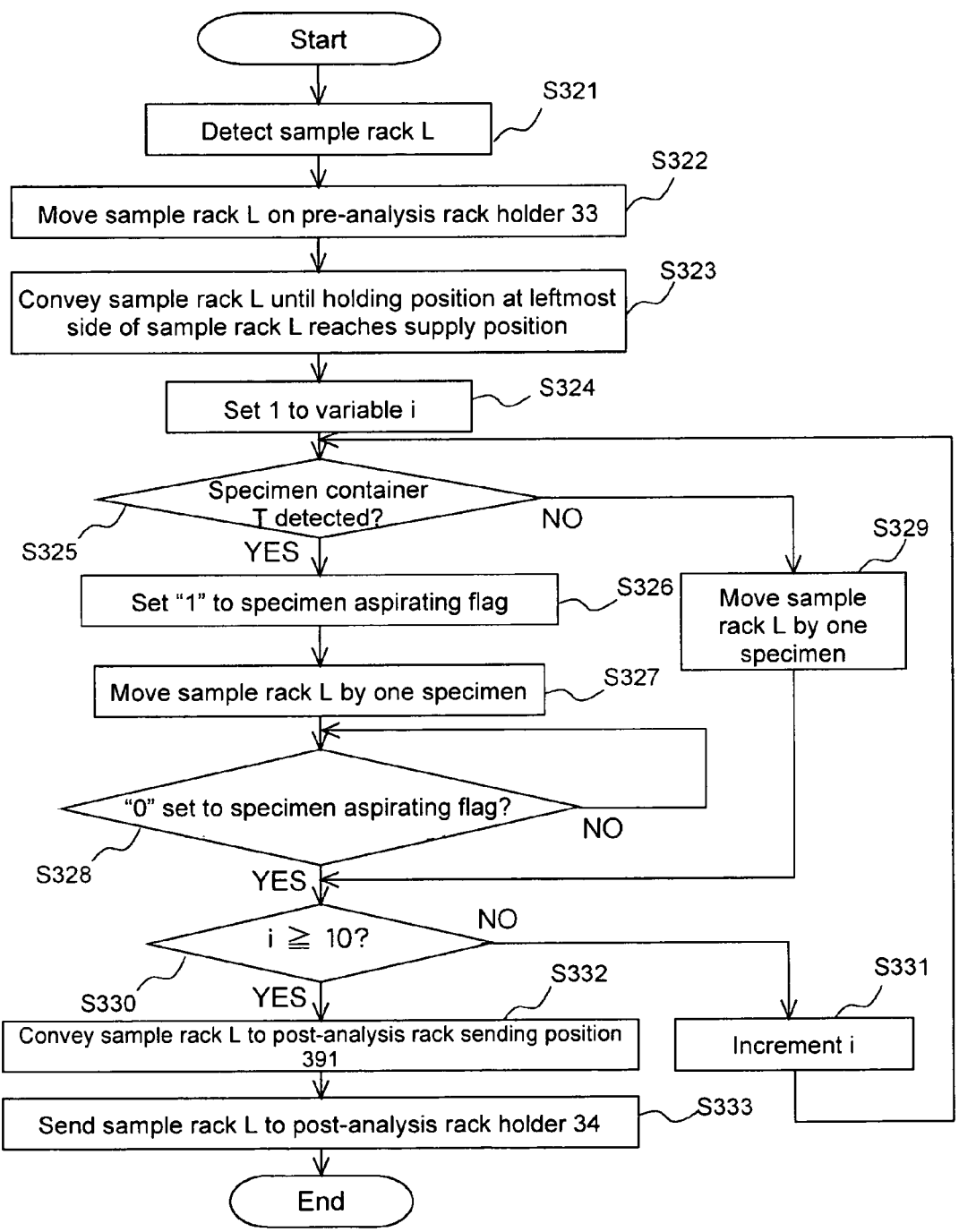
FIG. 14 is a flowchart showing a flow of the control process of the first conveyance mechanism in the second conveyance control mode by the information processing unit of the blood cell analyzer according to the embodiment.

FIG. 14 is a flowchart showing a flow of the control process of the first conveyance mechanism 31 in the second conveyance control mode by the information processing unit 52 of the blood cell analyzer 5. In the second conveyance control mode, the user mounts a plurality of sample racks L on the pre-analysis rack holder 33 of the first conveyance mechanism 31 by hand. In this case, the sample rack L mounted at the rack detection position 33a is detected by the rack sensor 37 (step S321). In the CPU 521a, the process of step S322 is called out when an event in which the sample rack L is detected by the rack sensor 37 occurs.

In step S322, the CPU 521a operates the rack sending portion 33b by driving the stepping motor 33c, thereby moving the sample rack L on the pre-analysis rack holder 33 (step S322). Thereafter, the CPU 521a executes the processes of steps S323 to S333, but such processes are similar to the processes of steps S304 to S314 described above, and thus the description thereof will be omitted.

In this case, as the second conveyance mechanism 32 does not operate, the sample rack L accommodating the specimen, which analysis is completed, is sequentially sent to the post-analysis rack holder 34 by the rack sending portion 39, and such plurality of sample racks L are stored in the post-analysis rack holder 34.

Figure 15A:
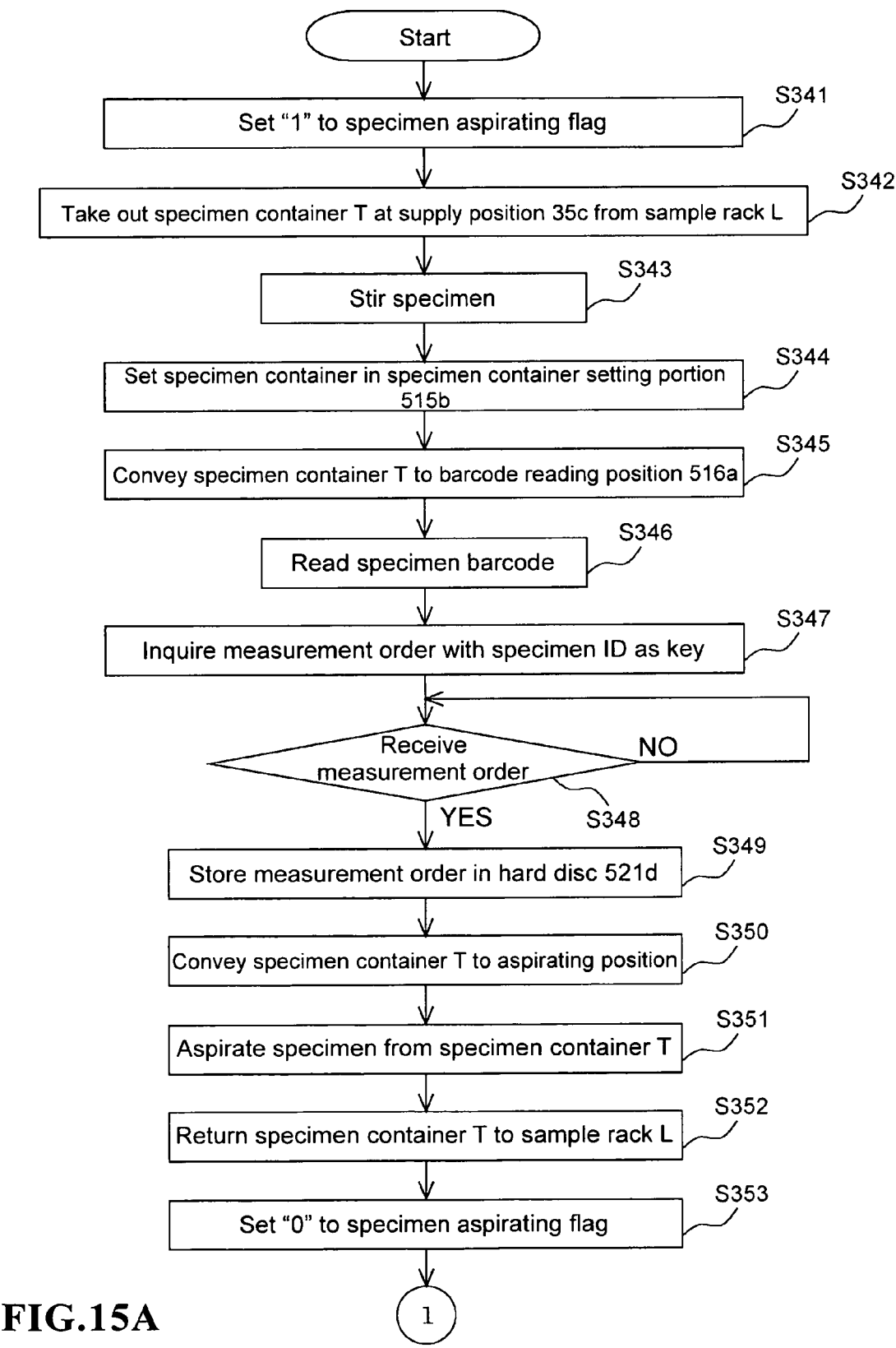
FIG. 15A is a flowchart (first half) showing a procedure of the analyzing process of the specimen by the information processing unit of the blood cell analyzer according to the embodiment.
Figure 15B:
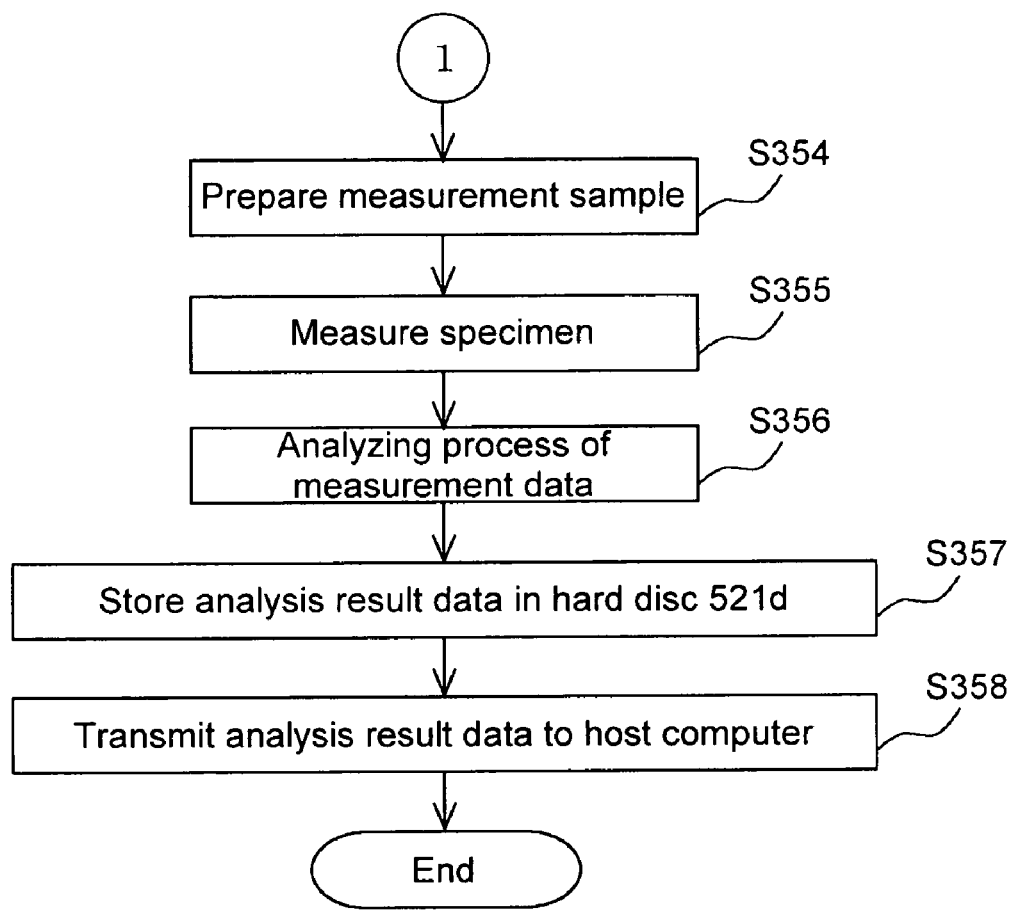
FIG. 15B is a flowchart (second half) showing a procedure of the analyzing process of the specimen by the information processing unit of the blood cell analyzer according to the embodiment.

The analyzing operation of the specimen by the blood cell analyzer 5 will now be described. FIGS. 15A and 15B are flowcharts showing a procedure of the analyzing operation of the specimen by the blood cell analyzer 5 according to the present embodiment. First, the CPU 521a of the information processing unit 52 periodically checks the specimen aspirating flag of the RAM 521c. In the CPU 521a, the process of step S342 is called out when an event in which "1" is set to the specimen aspirating flag occurs (step S341).

In step S342, the CPU 521a controls the specimen container conveyance portion 515 to take out the specimen container T at the supply position 35c from the sample rack L (step S342), and controls the hand portion 515a to oscillate the specimen container T and stir the specimen inside (step S343). The CPU 521a then controls the hand portion 515a to set the specimen container T at the specimen container setting portion 515b (step S344), and then controls the specimen container conveyance portion 515 to convey the specimen container T to the barcode reading position 516a (step S345).

The CPU 521a reads the specimen barcode of the specimen container T with the barcode readout portion 516, and acquires the specimen ID (step S346). Furthermore, the CPU 521a causes the communication interface 521g to transmit the order request data containing the specimen ID to the host computer 9 (step S347), and inquires the measurement order. Thereafter, the CPU 521a waits for the reception of the measurement data (NO in step 348), and stores the received measurement order in the hard disc 521d (step S349) when receiving the measurement order transmitted from the host computer 9 with the communication interface 521g of the information processing unit 52 (YES in step S348).

The CPU 521a controls the specimen container conveyance portion 515 to convey the specimen container T to the aspirating position (step S350), and controls the specimen aspirating portion 511 to aspirate the specimen of an amount necessary for the measurement items contained in the stored measurement order from the specimen container T (step S351). After the aspiration of the specimen is completed, the CPU 521a controls the specimen container conveyance portion 515 to return the specimen container T to the sample rack L (step S352), and sets "0" to the specimen aspirating flag (step S353). The sample rack L is thereby conveyed by the rack conveyance portion 35, as described above.

The CPU 521a then controls the sample preparing portion 512 to prepare the measurement sample according to the measurement item (step S354), supplies the measurement sample to the detecting portion 513, and performs the measurement of the specimen by the detecting portion 513 (step S355). The CPU 521a thereby acquires the measurement data output from the detecting portion 513. The CPU 521a executes the analyzing process of the measurement data (step S356), classifies the blood cells contained in the specimen and counts the number of blood cells for every type, and creates a scattergram in which the classified blood cells are colored by type. The analysis result data generated by the analyzing process of the measurement data is stored in the hard disc 521a with the patient information and the like contained in the measurement order (step S357), and also transmitted to the host computer 9 (step S358). The host computer 9 integrates the analysis result data to the measurement data and stores the same in the hard disc. After the process of step S358 is completed, the CPU 521a terminates the process.

<Operation of Specimen Conveyance Device 301>

The sample rack L sent from the specimen conveyance device 3 positioned on the most downstream side in the conveyance direction is introduced to the rack slider 303. Although the details are omitted, the rack slider 303 accepts the instruction from the system control device 8, and sends the sample rack L to either the measurement line 302a or the skip line 302b of the conveyor 302. When the sample rack L is carried in the measurement line 302a, the controller of the conveyor 302 operates the measurement line 302a, and conveys the sample rack L such that the specimen container T of the smear producing target is positioned at the supply position of supplying the specimen to the smear producing device 6. After the supply of specimen to the smear producing device 6 is completed, the measurement line 302a is further driven, and the sample rack L is carried out to the specimen accommodating device 4. When the sample rack L is carried in the skip line 302b, the controller of the conveyor 302 operates the skip line 302b, and conveys the sample rack L on the skip line 302 to carry out the sample rack L to the specimen accommodating device 4.

<Operation of Specimen Accommodating Device 4>

The sample rack L sent from the specimen conveyance device 301 is introduced to the specimen accommodating device 4. The specimen accommodating device 4 conveys and accommodates the sample rack L on the rack mounting portion.

According to such configuration, since the information processing unit 52 can control the first conveyance mechanism 31 independent from the controller 300 even when the second conveyance mechanism 32 cannot be operated such as the case where failure or abnormality occurs in the controller 300 or the second conveyance mechanism 32 of the specimen conveyance device 3, or the system control device 8, or the case where the system control device 8 is not activating, the specimen can be analyzed using the blood cell analyzer 5 and the first conveyance mechanism 31.

In particular, when failure or abnormality occurs in the controller 300 (shown in FIG. 4), the second conveyance mechanism 32, or the system control device 8, the control operation of the controller 300 stops and the service man or the user needs to perform repair or restoration task. The specimen processing system according to the present embodiment is useful in that continuous measurement of the specimen by using the conveyance mechanism can be performed in such case.

Since the first conveyance control mode and the second conveyance control mode are switchable by the user, when failure or abnormality occurs in the controller 300, the second conveyance mechanism 32, or the system control device 8 while operating the specimen processing system, the user can easily resume the analysis of the specimen by simply setting the second conveyance control mode. If the number of specimens to be analyzed is small, the analysis may be performed using only part of the specimen processing system without operating the entire specimen processing system. In such case, the specimen can be easily analyzed by activating one specimen conveyance device 3 (shown in FIGS. 1 and 4), one measurement unit 51 (shown in FIG. 1), and the information processing unit 52 (shown in FIG. 1), and having the user set the second conveyance control mode. Using the specimen processing system in such manner does not require the entire specimen processing system to be operated, and thus it is preferable from the standpoint of saving power.

The specimen processing system according to the present embodiment starts the conveyance of the sample rack L (shown in FIGS. 3 and 4-5) by the first conveyance mechanism 31 with the conveyance start instruction data transmitted from the controller 300 to the information processing unit 52 (shown in FIG. 1) as the trigger when the first conveyance control mode is set, so that the controller 300 (shown in FIG. 4) and the information processing unit 52 can execute the conveyance control in synchronization, and the first conveyance mechanism 31 and the second conveyance mechanism 32 can be smoothly operated. If the second conveyance control mode is set, the conveyance of the sample rack L by the first conveyance mechanism 31 starts with the detection of the sample rack L on the pre-analysis rack holder 33 by the rack sensor 37 as the trigger, so that the information processing unit 52 can control the first conveyance mechanism 31 independent from the controller 300.

The specimen processing system according to the present embodiment is configured such that the pre-analysis rack holder 33 (shown in FIG. 4) capable of storing a plurality of sample racks L (shown in FIGS. 3 and 4-5) is arranged in the first conveyance mechanism 31, the sample rack L mounted on the pre-analysis rack holder 33 is automatically conveyed, and the specimen accommodated in such sample racks L is measured, and thus the user can simply mount a plurality of sample racks L on the pre-analysis rack holder 33 to analyze the specimen accommodated in such sample racks L when the second conveyance control mode is set.

Other Embodiments

In the embodiment described above, the first conveyance mechanism 31 is controlled by the information processing unit 52 of the blood cell analyzer 5, but this is not the sole case. A controller dedicated to the first conveyance mechanism 31 may be arranged separate from the information processing unit 52 and the controller 300.

In the embodiment described above, a configuration of arranging the controller 300 dedicated to the second conveyance mechanism 32 has been described, but this is not the sole case. The system control device 8 may control the second conveyance mechanism 32.

In the embodiment described above, either one of the first conveyance control mode or the second conveyance control mode can be set, wherein the information processing unit 52 and the controller 300 cooperate to control the first conveyance mechanism 31 and the second conveyance mechanism 32 when the first conveyance control mode is set, and the information processing unit 52 controls the first conveyance mechanism independent from the controller 300 when the second conveyance control mode is set, but this is not the sole case. Regardless of whether or not the controller 300 is controlling the second conveyance mechanism, the information processing unit 52 may control the first conveyance mechanism 31 independent from the controller 300. This can be realized, for example, by starting the conveyance of the sample rack L by the first conveyance mechanism 31 with the detection of the sample rack L on the pre-analysis rack holder 33 by the rack sensor 37 as the trigger even if the controller 300 is controlling the second conveyance mechanism.

In the embodiment described above, the conveyance start instruction data is transmitted from the controller 300 to the information processing unit 52, the information processing unit 52 receiving the same controls the first conveyance mechanism 31 to convey the sample rack L, and the measurement order of the specimen is acquired using the specimen ID acquired by reading the specimen barcode of the specimen container T held at the sample rack L, but this is not the sole case, and the following configuration may be adopted. The system control device 8 collectively acquires the measurement orders of a plurality of specimens from the host computer 9. The barcode reader is arranged at the specimen inserting device 2, the rack ID and the specimen ID are read for every sample rack L by such barcode reader, and the rack ID and the specimen ID are transmitted to the system control device 8 in place of the rack sequential number by the specimen inserting device 2. The system control device 8 searches for the corresponding measurement order with the received specimen ID as the key, and transmits the measurement order to the specimen conveyance device 3 for every sample rack L. When instructing the start of conveyance of the first conveyance mechanism 31 to the information processing unit 52, the controller 300 transmits the conveyance start instruction data including the received measurement order to the information processing unit 52. When receiving the conveyance start instruction data, the information processing unit 52 starts the conveyance of the sample rack L by the first conveyance mechanism 31, aspirate the specimen according to the measurement order obtained in such manner, and performs the measurement of the specimen.

In the embodiment described above, a configuration in which the first conveyance mechanism 31, 31 respectively arranged in the two adjacent specimen conveyance devices 3, 3 cannot exchange the sample rack with respect to each other has been described, but is not limited thereto. The plurality of first conveyance mechanism may be controlled such that the specimen can be exchanged between the adjacent first conveyance mechanisms when the first conveyance mechanism of the two adjacent specimen conveyance devices are connected so that exchange of sample rack L can be performed, and the second conveyance control mode is set. The sample rack L thus can be conveyed among the plurality of first conveyance mechanisms and the specimen can be automatically supplied to the plurality of measurement units 51 even if the second conveyance mechanism 32 is unusable.

The information processing unit 52 may control not only the first conveyance mechanism 31 but also the second conveyance mechanism 32 when the second conveyance control mode is set. For instance, the information processing unit 52 may control the second conveyance mechanism 32 such that the sample rack L carried out from the device of the pre-stage to the second conveyance mechanism 32 is carried in and sent to the pre-analysis rack holder 33 when the second conveyance control mode is set, or the information processing unit 52 may control the second conveyance mechanism 32 such that the sample rack L sent from the rack conveyance portion 35 to the post-analysis rack holder 34 is sent from the post-analysis rack holder 34 to the rack conveyance portion 321 and the sample rack L sent to the rack conveyance portion 321 is carried out to the device of the post-stage. Thus, the sample rack L can be conveyed among the plurality of second conveyance mechanism 32, 32 and the specimen can be automatically supplied to the plurality of measurement units 51 even if the controller 300 is inoperable.

In the embodiment described above, a configuration of controlling the first conveyance mechanism by having the CPU execute the control computer program of the first conveyance mechanism has been described, but is not limited thereto. The control process of the first conveyance mechanism may be executed by a dedicated hardware such as FPGA or ASIC capable of executing a process similar to the control program of the first conveyance mechanism. Similarly, the control process of the second conveyance mechanism may be executed by a dedicated hardware such as FPGA or ASIC capable of executing a process similar to the control program of the second conveyance mechanism.

In the embodiment described above, a configuration in which the specimen processing system includes the blood cell analyzer 5 (shown in FIG. 1) for classifying the blood cells contained in the specimen and counting the blood cells for every blood cell type has been described, but is not limited thereto. The specimen processing system may include a specimen analyzer other than the blood cell analyzer such as immune analyzer, blood coagulation measurement device, biochemical analyzer, and urine analyzer, and the blood specimen or the urine specimen may be conveyed to the measurement unit of the relevant specimen analyzer.

In the embodiment described above, a configuration in which the specimen conveyance devices 3, 301 convey the sample rack L including ten holders (holding positions) for holding the specimen container T has been described, but is not limited thereto. The specimen conveyance device may convey the sample rack including a plurality of holders other than ten such as three or five holders, or the specimen conveyance device may convey the sample rack capable of holding only one specimen container T.

In the embodiment described above, a configuration in which all processes of the computer program 524*a* are executed by a single computer 52*a* has been described, but this is not the sole case, and a distributed system of executing the processes similar to the computer program 524*a* in a distributed manner by a plurality of devices (computers) may be adopted.

What is claimed is:

1. A specimen processing device comprising:
   a first specimen processing unit and a second specimen processing unit for processing specimens;
   a first specimen conveyance device and a second specimen conveyance device corresponding to the first specimen processing unit and the second specimen processing unit, respectively, wherein the first specimen conveyance device is arranged on an upstream side of conveyance with respect to the second specimen conveyance device; and
   a first control device and a second control device for controlling at least the first specimen conveyance device, wherein
   the first specimen conveyance device comprises:
   a first conveyance mechanism for conveying specimens from a first accepting position for accepting the specimens carried into the first conveyance mechanism to a specimen supply position for supplying the specimens to the first specimen processing unit; and
   a second conveyance mechanism for sending specimens from a second accepting position for accepting the specimens carried into the second conveyance mechanism to any one of the first accepting position and a carrying out position for carrying out the specimens to the second specimen conveyance device from the second conveyance mechanism, wherein
   the first control device is configured to control the first conveyance mechanism, and
   the second control device is configured to control the second conveyance mechanism.

2. The specimen processing device according to claim 1, wherein the first control device is configured to control the first conveyance mechanism independent from the second control device.

3. The specimen processing device according to claim 2, wherein the first control device is configured to control the first conveyance mechanism when the second control device is stopping a control of the second conveyance mechanism.

4. The specimen processing device according to claim 3, wherein the first control device is configured to switch between a first conveyance control mode set when the second control device operates, and a second conveyance control mode set when the second control device is stopping the control of the second conveyance mechanism.

5. The specimen processing device according to claim 4, wherein
   the second control device is configured to transmit a conveyance start instruction signal for instructing start of conveyance of specimens to the first control device; and
   the first control device includes a specimen detector for detecting specimens, the conveyance of specimens being started when receiving the conveyance start instruction signal from the second control device if the first conveyance control mode is set, and the conveyance of specimens being started when at least one of specimens is detected by the specimen detector if the second conveyance control mode is set.

6. The specimen processing device according to claim 5, wherein
   the first and second specimen processing units each comprise a specimen measurement unit for measuring specimens with respect to a plurality of measurement items; and
   the second control device is configured to acquire a measurement order including designation of measurement items, and transmitting the conveyance start instruction signal including the acquired measurement order to the first control device.

7. A specimen processing device comprising:
   a first specimen processing unit and a second specimen processing unit for processing specimens;
   a first specimen conveyance device and a second specimen conveyance device corresponding to the first specimen processing unit and the second specimen processing unit, respectively, wherein the first specimen conveyance device is arranged on an upstream side of conveyance with respect to the second specimen conveyance device; and
   a first control device and a second control device for controlling at least the first specimen conveyance device, wherein
   the first specimen conveyance device comprises:
   a first conveyance mechanism for conveying specimens from a first accepting position for accepting the specimens carried into the first conveyance mechanism to a specimen supply position for supplying the specimens to the first specimen processing unit
   wherein the first conveyance mechanism includes a storage portion for storing specimens, and is configured to convey the specimens stored in the storage portion through the specimen supply position, and wherein the first accepting position is located in the storage portion; and
   a second conveyance mechanism for sending specimens from a second accepting position for accepting the specimens carried into the second conveyance mechanism to any one of the first accepting position and a carrying out position for carrying out the specimens to the second specimen conveyance device from the second conveyance mechanism, wherein
   the first control device is configured to control the first conveyance mechanism, and
   the second control device is configured to control the second conveyance mechanism.

8. The specimen processing device according to claim 1, wherein
   the first conveyance mechanism is configured to convey to a sending position for sending the specimens to the carrying out position of the second conveyance mechanism.

9. The specimen processing device according to claim 1, wherein the first control device is configured to control at least the first specimen processing unit.

10. A specimen processing device comprising:
    a first specimen processing unit and a second specimen processing unit for processing specimens;
    a first specimen conveyance device and a second specimen conveyance device corresponding to the first specimen processing unit and the second specimen processing unit, respectively, wherein the first specimen conveyance device is arranged on an upstream side of conveyance with respect to the second specimen conveyance device; and
    a first control device and a second control device for controlling at least the first specimen conveyance device, wherein the first specimen conveyance device comprises:

a first conveyance mechanism for conveying specimens from a first accepting position for accepting the specimens carried into the first conveyance mechanism to a specimen supply position for supplying the specimens to the first specimen processing unit; and a second conveyance mechanism for sending specimens from a second accepting position for accepting the specimens carried into the second conveyance mechanism to any one of the first accepting position and a carrying out position for carrying out the specimens to the second specimen conveyance device from the second conveyance mechanism, wherein the first control device is configured to control the first conveyance mechanism, and the second control device is configured to control the second conveyance mechanism, wherein the second specimen conveyance device comprises:

a first conveyance mechanism for conveying specimens from a first accepting position for accepting the specimens carried into the first conveyance mechanism to a second specimen supply position for supplying the specimens to the second specimen processing unit; and a second conveyance mechanism for sending specimens from a second accepting position for accepting the specimens carried into the second conveyance mechanism to anyone of the first accepting position and a second carrying out position for carrying out the specimens from the second specimen conveyance device, and wherein the first control device is configured to control the first conveyance mechanism, and the second control device is configured to control the second conveyance mechanism.

11. The specimen processing device according to claim 10, further comprising a third control device for determining a conveying destination of specimens from the plurality of specimen processing units.

\* \* \* \* \*